(12) United States Patent
Arnault De La Menardiere et al.

(10) Patent No.: US 9,526,642 B2
(45) Date of Patent: Dec. 27, 2016

(54) VASCULAR IMPLANTS AND METHODS OF FABRICATING THE SAME

(75) Inventors: Brice Maxime Arnault De La Menardiere, Santa Cruz, CA (US); Frederich Albert Lim Alavar, San Jose, CA (US); Robert C. LaDuca, Santa Cruz, CA (US); Paul A. LaDuca, Little Elm, TX (US); Carol LaSalle, Redwood City, CA (US)

(73) Assignee: Taheri LaDuca LLC, Santa Cruz, CA (US)

( * ) Notice: Subject to any disclaimer, the term of this patent is extended or adjusted under 35 U.S.C. 154(b) by 0 days.

(21) Appl. No.: 12/029,147

(22) Filed: Feb. 11, 2008

(65) Prior Publication Data

US 2009/0043373 A1 Feb. 12, 2009

Related U.S. Application Data

(60) Provisional application No. 60/889,157, filed on Feb. 9, 2007.

(51) Int. Cl.
| | | |
|---|---|---|
| *A61F 2/44* | (2006.01) | |
| *A61F 2/90* | (2013.01) | |
| *A61F 2/07* | (2013.01) | |
| *A61F 2/856* | (2013.01) | |
| *A61F 2/24* | (2006.01) | |

(52) U.S. Cl.
CPC . *A61F 2/90* (2013.01); *A61F 2/07* (2013.01); *A61F 2/856* (2013.01); *A61F 2/2418* (2013.01); *A61F 2/2451* (2013.01); *A61F 2002/075* (2013.01); *A61F 2220/0016* (2013.01); *A61F 2220/0033* (2013.01); *A61F 2220/0041* (2013.01); *A61F 2220/0066* (2013.01); *A61F 2220/0075* (2013.01); *A61F 2250/0006* (2013.01)

(58) Field of Classification Search
CPC .... A61F 2002/075; A61F 2/07; A61F 2/2418; A61F 2/2451; A61F 2220/0016; A61F 2220/0041; A61F 2220/0033; A61F 2220/0066; A61F 2220/0075
USPC .......... 623/1.15, 1.16, 1.35, 1.4, 1.39, 1.31, 623/1.37; 606/200
See application file for complete search history.

(56) References Cited

U.S. PATENT DOCUMENTS

| | | |
|---|---|---|
| 3,976,071 A | 8/1976 | Sadek |
| 4,335,094 A | 6/1982 | Mosbach |
| 4,345,588 A | 8/1982 | Widder et al. |

(Continued)

FOREIGN PATENT DOCUMENTS

| | | |
|---|---|---|
| DE | 19703482 | 8/1988 |
| EP | 1472990 | 11/2004 |

(Continued)

OTHER PUBLICATIONS

U.S. Appl. No. 11/274,623, filed Nov. 14, 2005 in the name of LaDuca et al., Final Office Action mailed Aug. 26, 2009.

(Continued)

*Primary Examiner* — Julie A Szpira
(74) *Attorney, Agent, or Firm* — Levine Bagade Han LLP

(57) ABSTRACT

The present invention is directed to vascular implants and methods for fabricating the same. The implantable devices include but are not limited to stents, grafts and stent grafts. In many embodiments, the devices include one or more side branch lumens interconnected with the main lumen.

13 Claims, 14 Drawing Sheets

(56) References Cited

U.S. PATENT DOCUMENTS

| | | |
|---|---|---|
| 4,357,259 A | 11/1982 | Senyei et al. |
| 4,501,263 A | 2/1985 | Harbuck |
| 4,501,726 A | 2/1985 | Schroder et al. |
| 4,830,003 A | 5/1989 | Wolff et al. |
| 4,832,686 A | 5/1989 | Anderson |
| 4,871,716 A | 10/1989 | Longo et al. |
| 4,872,874 A | 10/1989 | Taheri |
| 4,883,666 A | 11/1989 | Sabel et al. |
| 4,894,231 A | 1/1990 | Moreau et al. |
| 4,897,268 A | 1/1990 | Tice et al. |
| 4,902,508 A | 2/1990 | Badylak et al. |
| 4,904,479 A | 2/1990 | Illum |
| 4,936,281 A | 6/1990 | Stasz |
| 4,956,178 A | 9/1990 | Badylak et al. |
| 5,000,185 A | 3/1991 | Yock |
| 5,026,377 A | 6/1991 | Burton et al. |
| 5,042,707 A | 8/1991 | Taheri |
| 5,042,976 A | 8/1991 | Ishitsu et al. |
| 5,067,491 A | 11/1991 | Taylor, II et al. |
| 5,069,216 A | 12/1991 | Groman et al. |
| 5,112,457 A | 5/1992 | Marchant |
| 5,163,952 A | 11/1992 | Froix |
| 5,176,907 A | 1/1993 | Leong |
| 5,206,159 A | 4/1993 | Cohen et al. |
| 5,225,282 A | 7/1993 | Chagnon et al. |
| 5,275,826 A | 1/1994 | Badylak et al. |
| 5,286,254 A | 2/1994 | Shapland et al. |
| 5,342,348 A | 8/1994 | Kaplan |
| 5,356,433 A | 10/1994 | Rowland et al. |
| 5,368,557 A | 11/1994 | Nita et al. |
| 5,409,000 A | 4/1995 | Imran |
| 5,411,550 A | 5/1995 | Herweck et al. |
| 5,415,664 A | 5/1995 | Pinchuk |
| 5,419,760 A | 5/1995 | Narciso, Jr. |
| 5,427,767 A | 6/1995 | Kresse et al. |
| 5,447,724 A | 9/1995 | Helmus et al. |
| 5,463,010 A | 10/1995 | Hu et al. |
| 5,464,449 A | 11/1995 | Ryan et al. |
| 5,464,450 A | 11/1995 | Buscemi et al. |
| 5,464,650 A | 11/1995 | Berg et al. |
| 5,484,584 A | 1/1996 | Wallace et al. |
| 5,500,013 A | 3/1996 | Buscemi et al. |
| 5,543,158 A | 8/1996 | Gref et al. |
| 5,545,208 A | 8/1996 | Wolff et al. |
| 5,551,954 A | 9/1996 | Buscemi et al. |
| 5,554,389 A | 9/1996 | Badylak et al. |
| 5,569,463 A | 10/1996 | Helmus et al. |
| 5,591,227 A | 1/1997 | Dinh et al. |
| 5,609,627 A * | 3/1997 | Goicoechea et al. ......... 128/898 |
| 5,609,629 A | 3/1997 | Fearnot et al. |
| 5,617,878 A | 4/1997 | Taheri |
| 5,624,411 A | 4/1997 | Tuch |
| 5,637,113 A | 6/1997 | Tartaglia et al. |
| 5,649,977 A | 7/1997 | Campbell |
| 5,653,743 A | 8/1997 | Martin |
| 5,656,297 A | 8/1997 | Bernstein et al. |
| 5,669,924 A | 9/1997 | Shaknovich |
| 5,676,696 A | 10/1997 | Marcade |
| 5,676,697 A | 10/1997 | McDonald |
| 5,679,400 A | 10/1997 | Tuch |
| 5,693,083 A | 12/1997 | Baker et al. |
| 5,700,269 A | 12/1997 | Pinchuk et al. |
| 5,700,286 A | 12/1997 | Tartaglia et al. |
| 5,723,004 A | 3/1998 | Dereume et al. |
| 5,725,494 A | 3/1998 | Brisken |
| 5,728,062 A | 3/1998 | Brisken |
| 5,735,811 A | 4/1998 | Brisken |
| 5,741,325 A | 4/1998 | Chaikof et al. |
| 5,755,735 A | 5/1998 | Richter et al. |
| 5,769,883 A | 6/1998 | Buscemi et al. |
| 5,824,049 A | 10/1998 | Ragheb et al. |
| 5,824,064 A | 10/1998 | Taheri |
| 5,837,008 A | 11/1998 | Berg et al. |
| 5,843,167 A | 12/1998 | Dwyer et al. |
| 5,843,169 A | 12/1998 | Taheri |
| 5,843,172 A | 12/1998 | Yan |
| 5,851,231 A | 12/1998 | Wolff et al. |
| 5,876,452 A | 3/1999 | Athanasiou et al. |
| 5,879,808 A | 3/1999 | Wary et al. |
| 5,891,108 A | 4/1999 | Leone et al. |
| 5,893,840 A | 4/1999 | Hull et al. |
| 5,928,145 A | 7/1999 | Ocali et al. |
| 5,948,017 A | 9/1999 | Taheri |
| 5,951,586 A | 9/1999 | Berg et al. |
| 5,968,092 A | 10/1999 | Buscemi et al. |
| 5,972,027 A | 10/1999 | Johnson |
| 5,980,551 A | 11/1999 | Summers et al. |
| 5,980,566 A | 11/1999 | Alt et al. |
| 5,984,955 A | 11/1999 | Wisselink |
| 5,993,481 A | 11/1999 | Marcade et al. |
| 5,997,468 A | 12/1999 | Wolff et al. |
| 6,017,363 A | 1/2000 | Hojeibane |
| 6,030,414 A | 2/2000 | Taheri |
| 6,031,375 A | 2/2000 | Atalar et al. |
| 6,033,434 A | 3/2000 | Borghi |
| 6,048,360 A | 4/2000 | Khosravi et al. |
| 6,051,020 A | 4/2000 | Goicoechea et al. |
| 6,051,276 A | 4/2000 | Wary et al. |
| 6,059,824 A | 5/2000 | Taheri |
| 6,063,101 A | 5/2000 | Jacobsen et al. |
| 6,071,305 A | 6/2000 | Brown et al. |
| 6,074,362 A * | 6/2000 | Jang et al. ................... 604/104 |
| 6,074,398 A | 6/2000 | Leschinsky |
| 6,077,296 A | 6/2000 | Shokoohi et al. |
| 6,077,297 A | 6/2000 | Robinson et al. |
| 6,096,070 A | 8/2000 | Ragheb et al. |
| 6,099,548 A | 8/2000 | Taheri |
| 6,099,561 A | 8/2000 | Alt |
| 6,099,567 A | 8/2000 | Badylak et al. |
| 6,106,549 A | 8/2000 | Taheri |
| 6,129,738 A | 10/2000 | Lashinski et al. |
| 6,183,504 B1 | 2/2001 | Inoue |
| 6,183,509 B1 | 2/2001 | Dibie |
| 6,187,033 B1 | 2/2001 | Schmitt et al. |
| 6,187,036 B1 | 2/2001 | Shaolian et al. |
| 6,210,429 B1 | 4/2001 | Vardi et al. |
| 6,228,052 B1 | 5/2001 | Pohndorf |
| 6,238,432 B1 | 5/2001 | Parodi |
| 6,258,115 B1 * | 7/2001 | Dubrul ......................... 606/200 |
| 6,306,145 B1 | 10/2001 | Leschinsky |
| 6,306,164 B1 | 10/2001 | Kujawski |
| 6,325,826 B1 | 12/2001 | Vardi et al. |
| 6,355,061 B1 | 3/2002 | Quiachon et al. |
| 6,379,710 B1 | 4/2002 | Badylak |
| 6,383,213 B2 | 5/2002 | Wilson et al. |
| 6,409,750 B1 | 6/2002 | Hyodoh et al. |
| 6,440,161 B1 | 8/2002 | Madrid et al. |
| 6,471,722 B1 | 10/2002 | Inoue |
| 6,478,817 B2 | 11/2002 | Schmitt et al. |
| 6,520,988 B1 | 2/2003 | Colombo et al. |
| 6,533,811 B1 | 3/2003 | Ryan et al. |
| 6,551,350 B1 | 4/2003 | Thornton et al. |
| 6,599,302 B2 | 7/2003 | Houser et al. |
| 6,641,606 B2 | 11/2003 | Ouriel et al. |
| 6,673,107 B1 | 1/2004 | Brandt et al. |
| 6,695,877 B2 | 2/2004 | Brucker et al. |
| 6,723,116 B2 | 4/2004 | Taheri |
| 6,732,116 B2 | 5/2004 | Banerjee et al. |
| 6,733,522 B2 | 5/2004 | Schmitt et al. |
| 6,740,112 B2 * | 5/2004 | Yodfat et al. .................. 623/1.1 |
| 6,749,628 B1 | 6/2004 | Callol et al. |
| 6,761,734 B2 | 7/2004 | Suhr |
| 6,770,090 B2 | 8/2004 | Gantt et al. |
| 6,814,752 B1 | 11/2004 | Chuter |
| 6,824,558 B2 | 11/2004 | Parodi |
| 6,849,087 B1 | 2/2005 | Chuter |
| 6,918,925 B2 * | 7/2005 | Tehrani ........................ 623/1.11 |
| 6,942,640 B2 | 9/2005 | Kokish |
| 6,974,471 B2 * | 12/2005 | Van Schie et al. .......... 623/1.12 |
| 7,014,653 B2 | 3/2006 | Ouriel et al. |
| 7,056,323 B2 | 6/2006 | Mareiro et al. |
| 7,070,613 B2 | 7/2006 | Weber et al. |
| 7,105,014 B2 | 9/2006 | Murray, III |
| 7,105,020 B2 | 9/2006 | Greenberg et al. |

(56) References Cited

U.S. PATENT DOCUMENTS

| | | |
|---|---|---|
| 7,122,052 B2 | 10/2006 | Greenhalgh |
| 7,144,421 B2 | 12/2006 | Carpenter et al. |
| 7,189,257 B2 | 3/2007 | Schmitt et al. |
| 7,306,623 B2 | 12/2007 | Watson |
| 7,318,835 B2* | 1/2008 | Berra .................. 623/1.12 |
| 8,128,680 B2 | 3/2012 | Arnault De La Menardiere et al. |
| 2001/0003161 A1 | 6/2001 | Vardi et al. |
| 2001/0016768 A1* | 8/2001 | Wilson et al. ............ 623/1.11 |
| 2001/0025195 A1 | 9/2001 | Shaolian et al. |
| 2001/0027338 A1 | 10/2001 | Greenberg |
| 2003/0074049 A1 | 4/2003 | Hoganson et al. |
| 2003/0097170 A1 | 5/2003 | Friedrich et al. |
| 2003/0149466 A1 | 8/2003 | Gerberding |
| 2003/0199967 A1 | 10/2003 | Hartley et al. |
| 2003/0220680 A1 | 11/2003 | Kashyap |
| 2003/0229389 A1 | 12/2003 | Escano |
| 2004/0019375 A1* | 1/2004 | Casey et al. ............ 623/1.28 |
| 2004/0098114 A1* | 5/2004 | Wilson et al. ........... 623/1.35 |
| 2004/0102838 A1* | 5/2004 | Killion et al. .......... 623/1.16 |
| 2004/0106985 A1 | 6/2004 | Jang |
| 2004/0117003 A1 | 6/2004 | Ouriel et al. |
| 2004/0167613 A1* | 8/2004 | Yodfat et al. ........... 623/1.15 |
| 2004/0172121 A1 | 9/2004 | Eidenschink et al. |
| 2004/0215338 A1 | 10/2004 | Elkins et al. |
| 2004/0220660 A1 | 11/2004 | Shanley et al. |
| 2004/0230287 A1 | 11/2004 | Hartley et al. |
| 2004/0267352 A1 | 12/2004 | Davidson et al. |
| 2005/0010277 A1 | 1/2005 | Chuter |
| 2005/0033406 A1 | 2/2005 | Barnhart et al. |
| 2005/0043585 A1 | 2/2005 | Datta et al. |
| 2005/0049667 A1 | 3/2005 | Arbefeuille et al. |
| 2005/0049674 A1 | 3/2005 | Berra et al. |
| 2005/0085896 A1 | 4/2005 | Bonsignore et al. |
| 2005/0102018 A1 | 5/2005 | Carpenter et al. |
| 2005/0137680 A1* | 6/2005 | Ortiz et al. ............. 623/1.16 |
| 2005/0283220 A1* | 12/2005 | Gobran et al. ............ 623/1.4 |
| 2006/0100694 A1 | 5/2006 | Globerman |
| 2006/0129224 A1 | 6/2006 | Arbefeuille et al. |
| 2006/0142849 A1* | 6/2006 | Killion et al. .......... 623/1.31 |
| 2006/0155358 A1 | 7/2006 | LaDuca et al. |
| 2006/0155366 A1 | 7/2006 | LaDuca et al. |
| 2006/0229709 A1* | 10/2006 | Morris et al. ........... 623/1.31 |
| 2007/0055350 A1 | 3/2007 | Erickson et al. |
| 2007/0150051 A1 | 6/2007 | Arnault De La Menardiere et al. |
| 2007/0167955 A1 | 7/2007 | Arnault De La Menardiere et al. |
| 2007/0168020 A1* | 7/2007 | Brucker et al. .......... 623/1.35 |
| 2007/0179592 A1 | 8/2007 | Schaeffer |
| 2007/0219619 A1* | 9/2007 | Dieck et al. ............ 623/1.13 |
| 2009/0043373 A1 | 2/2009 | Arnault De La Menardiere et al. |
| 2009/0182405 A1 | 7/2009 | Arnault De La Menardiere et al. |

FOREIGN PATENT DOCUMENTS

| | | |
|---|---|---|
| JP | 2002-500920 | 1/2002 |
| JP | 2003-528689 | 9/2003 |
| JP | 2007-503923 | 3/2007 |
| JP | 2008-526379 | 7/2008 |
| WO | WO 98/06355 | 2/1998 |
| WO | WO 98/27893 | 7/1998 |
| WO | WO 98/31303 | 7/1998 |
| WO | WO 00/44309 | 8/2000 |
| WO | WO 02/39888 | 5/2002 |
| WO | WO 03/049644 | 6/2003 |
| WO | WO 2004/075789 | 9/2004 |
| WO | WO 2005/023149 | 3/2005 |
| WO | WO 2006/076325 | 7/2006 |
| WO | WO 2001/001957 | 1/2011 |

OTHER PUBLICATIONS

Kasyanov, V. et al., "Tannic acid mimicking dendrimers as small intestine submucosa stabilizing nanomordants," *Biomaterials*, 27:745-751, 2005, Elsevier Ltd.

U.S. Appl. No. 11/559,858, filed Nov. 14, 2006 in the name of LaDuca et al., Non-final Office Action mailed Sep. 8, 2009.

U.S. Appl. No. 11/274,623, filed Nov. 14, 2005 in the name of LaDuca et al., Non-final Office Action mailed Nov. 12, 2008.

U.S. Appl. No. 12/059,914, filed Mar. 31, 2008 in the name of LaDuca et al., non-final Office Action mailed Aug. 16, 2010.

Bezwada, Rao S., et al., "Poly(p-Dioxanone) and its copolymers," Handbook of Biodegradabie Polymers, pp. 29-61, 1997, Hardwood Academic Publishers, The Netherlands.

\* cited by examiner

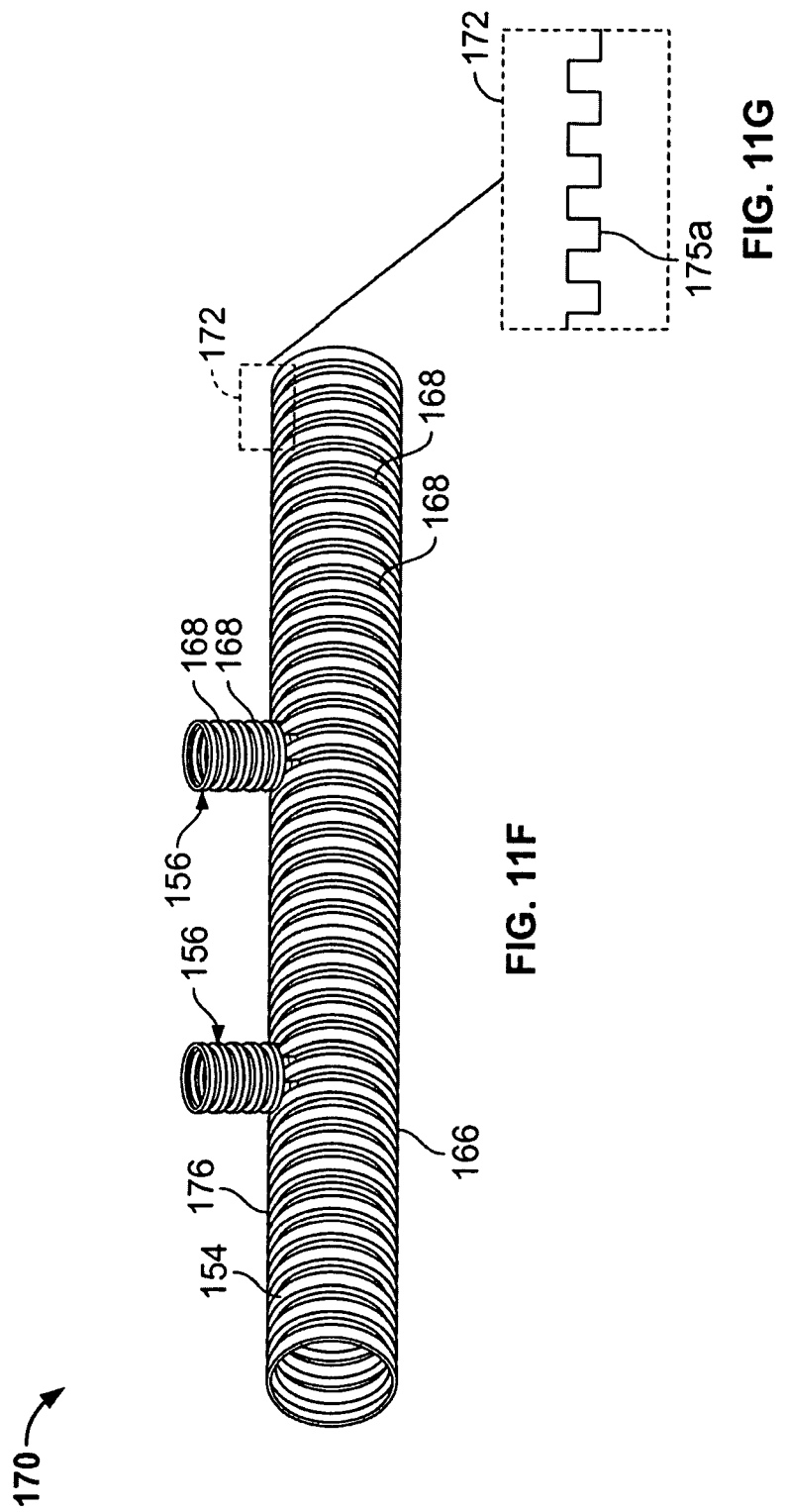

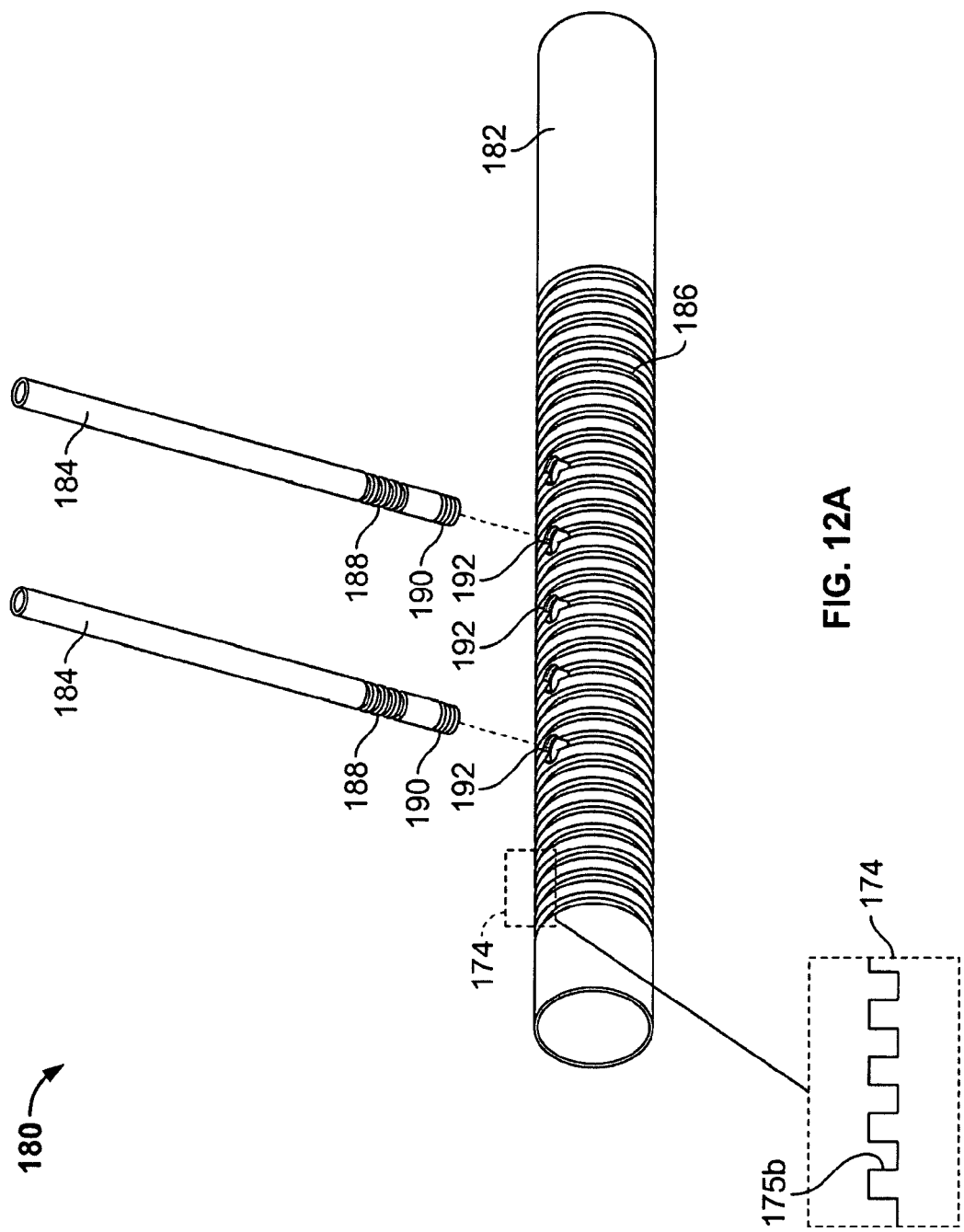

VASCULAR IMPLANTS AND METHODS OF FABRICATING THE SAME

CROSS-REFERENCE TO RELATED APPLICATIONS

The present application is a non-provisional of U.S. Provisional Patent Application. No. 60/889,157, filed on Feb. 9, 2007, the content of which is incorporated herein by reference in its entirety.

FIELD OF THE INVENTION

The present invention relates to the treatment of vascular disease, including for example aneurysms, ruptures, psuedoaneurysms, dissections, exclusion of vulnerable plaque and treatment of occlusive conditions, and more particularly, the invention is related to implantable devices and methods for fabricating the same.

BACKGROUND OF THE INVENTION

It is well known in the prior art to treat vascular disease with implantable stents and grafts. For example, it is well known in the art to interpose within a stenotic or occluded portion of an artery a stent capable of self-expanding or being balloon-expandable. Similarly, it is also well known in the prior art to use a graft or a stent graft to repair highly damaged or vulnerable portions of a vessel, particularly the aorta, thereby ensuring blood flow and reducing the risk of an aneurysm or rupture.

A more challenging situation occurs when it is desirable to use a stent, a graft or a stent graft at or around the intersection between a major artery (e.g., the abdominal aorta) and one or more intersecting arteries (e.g., the renal arteries). Use of single axial stents or grafts may effectively seal or block-off the blood flow to collateral organs such as the kidneys. U.S. Pat. No. 6,030,414 addresses such a situation, disclosing use of a stent graft having lateral openings for alignment with collateral blood flow passages extending from the primary vessel into which the stent graft is positioned. The lateral openings are pre-positioned within the stent based on identification of the relative positioning of the lateral vessels with which they are to be aligned. U.S. Pat. No. 6,099,548 discloses a multi-branch graft and a system for deploying it. Implantation of the graft is quite involved, requiring a discrete, balloon-deployable stent for securing each side branch of the graft within a designated branch artery. Additionally, a plurality of stylets is necessary to deliver the graft, occupying space within the vasculature and thereby making the system less adaptable for implantation into smaller vessels. Further, delivery of the graft and the stents requires access and exposure to each of the branch vessels into which the graft is to be placed by way of a secondary arteriotomy. These techniques, while effective, may be cumbersome and somewhat difficult to employ and execute, particularly where the implant site involves two or more vessels intersecting the primary vessel, all of which require engrafting.

The use of bifurcated stents for treating abdominal aortic aneurysms (AAA) is well known in the art. These stents have been developed specifically to address the problems that arise in the treatment of vascular defects and or disease at or near the site of a bifurcation. The bifurcated stent is typically configured in a "pant" design which comprises a tubular body or trunk and two tubular legs. Examples of bifurcated stents are provided in U.S. Pat. Nos. 5,723,004 and 5,755,735. Bifurcated stents may have either unitary configurations or modular configurations in which the components of the stent are interconnected in situ. In particular, one or both of the leg extensions are attachable to a main tubular body. Although the delivery of modular systems is less difficult due to the smaller sizes of the components, it is difficult to align and interconnect the legs with the body lumen with enough precision to avoid any leakage. On the other hand, while unitary stents reduce the probability of leakage, their larger structure is often difficult to deliver to a treatment site having a constrained geometry.

While the conventional bifurcated stents have been used somewhat successfully in treating AAA, they are not adaptable where the anatomy of the implant site is irregular, i.e., where the shape of the major artery, generally or at or around the branch artery intersection zone(s), is other than substantially straight, and/or where the anatomy of the implant is variable from patient to patient. The aortic arch is an example of the vascular anatomy that presents both of these challenges.

The highly curved anatomy of the aortic arch requires a stent that can accommodate various radii of curvature. More particularly, the stent wall is required to be adaptable to the tighter radius of curvature of the underside of the aortic arch without kinking while being able to extend or stretch to accommodate the longer topside of the arch without stretching the stent cells/wire matrix beyond its elastic capabilities.

Additionally, the variability of the anatomy of the aortic arch from person to person makes it a difficult location in which to place a stent graft. While the number of branch vessels originating from the arch is most commonly three, namely, the left subclavian artery, the left common carotid artery and the innominate artery, in some patients the number of branch vessels may be one, more commonly two and in some cases four, five or even six. Moreover, the spacing and angular orientation between the tributary vessels are variable from person to person.

Still yet, placing stents/grafts within the aortic arch presents additional challenges. The arch region of the aorta is subject to very high blood flow and pressures which make it difficult to position a stent graft without stopping the heart and placing the patient on cardiopulmonary bypass. Moreover, even if the stent graft is able to be properly placed, it must be secured in a manner to endure the constant high blood flow, pressures, and shear forces it is subjected to over time in order to prevent it from migrating or leaking. Additionally, the aorta undergoes relatively significant changes (of about 7%) in its diameter due to vasodilation and vasorestriction. As such, if an aortic arch graft is not able to expand and contract to accommodate such changes, there may be an insufficient seal between the graft and the aortic wall, subjecting it to a risk of migration and/or leakage.

In order to achieve alignment of a side branch stent or a lateral opening of the main stent with the opening of a branch vessel, a custom stent, designed and manufactured according to each patient's unique geometrical constraints, would be required. The measurements required to create a custom-manufactured stent to fit the patient's unique vascular anatomy could be obtained using spiral tomography, computed tomography (CT), fluoroscopy, or other vascular imaging system. However, while such measurements and the associated manufacture of such a custom stent could be accomplished, it would be time consuming and expensive. Furthermore, for those patients who require immediate intervention involving the use of a stent, such a customized stent is impractical. In these situations it would be highly desirable to have a stent which is capable of adjustability in situ while being placed and which can accommodate variable anatomy once placed. It would likewise be highly desirable to have the degree of adjustability sufficient to allow for a discrete number of stents to be manufactured in advance and available to accommodate the required range of sizes and configurations encountered.

Another disadvantage of conventional stents and stent grafts is the limitations in adjusting the position of or subsequently retrieving the stent or stent-graft once it has been deployed. Often, while the stent is being deployed, the final location of the delivered stent is determined not to be optimal for achieving the desired therapeutic effect. During deployment of self-expanding stents, the mode of deployment is either to push the stent out of a delivery catheter, or more commonly to retract an outer sheath while holding the stent in a fixed location relative to the vasculature. In either case the distal end of the stent is not attached to the catheter and, as such, is able to freely expand to its maximum diameter and seal with the surrounding artery wall. While this self-expanding capability is advantageous in deploying the stent, it presents the user with a disadvantage when desiring to remove or reposition the stent. Some designs utilize a trigger wire(s) to retain the distal end of the stent selectively until such time as full deployment is desired and accomplished by releasing the "trigger" wire or tether wire(s). The limitation of this design is the lack of ability to reduce the diameter of the entire length of stent. The significance of not being able to reduce the diameter of the stent while positioning it is that the blood flow is occluded by the fully expanded main body of the stent even though its distal end is held from opening.

Another disadvantage of conventional stent-grafts is the temporary disruption in blood flow through the vessel. In the case of balloon deployable stents and stent-grafts, expansion of the balloon itself while deploying the stent or stent-graft causes disruption of blood flow through the vessel. Moreover, in certain applications, a separate balloon is used at a location distal to the distal end of the stent delivery catheter to actively block blood flow while the stent is being placed. In the case of self-expanding stent-grafts, the misplacement of a stent graft may be due to disruption of the arterial flow during deployment, requiring the placement of an additional stent-graft in an overlapping fashion to complete the repair of the vessel. Even without disruptions in flow, the strong momentum of the arterial blood flow can cause a partially opened stent-graft to be pushed downstream by the high-pressure pulsatile impact force of the blood entering the partially deployed stent graft.

With the limitations of current stent grafts, there is clearly a need for improved stents and stent grafts for treating vascular disease and conditions affecting interconnecting vessels (i.e., vascular trees), and for improved means and methods for implanting them which address the drawbacks of the prior art.

SUMMARY OF THE INVENTION

The present invention is directed to vascular implants and methods for fabricating the same. The implantable devices generally include a tubular member or lumen, most typically in the form of a stent, a graft or a stent graft, where the device may further include one or more branching or transverse tubular members or lumens laterally extending from, the main or primary tubular member.

The implant sites addressable by the subject devices may be any tubular or hollow tissue lumen or organ; however, the most typical implant sites are vascular structures, particularly the aorta. Thus, devices of the invention are constructed such that they can address implant sites involving two or more intersecting tubular structures and, as such, are particularly suitable in the context of treating vascular trees such as the aortic arch and the infrarenal aorta.

The devices and their lumens are formed by interconnected cells where the cells are defined by starts which are preferably made of an elastic or superelastic material such that changes and adjustments can be made to various dimensions, orientations and shapes of the device lumens. As such, another feature of the present invention involves the reduction or expansion of a dimension, e.g., diameter and length, of one or more the device lumens. Typically, a change in one dimension is dependent upon or results in an opposite change in another dimension, i.e., when the diameter of the stent lumen is reduced, the length of the stent increases, and visa versa. The material construct of the devices further enables the one or more side branch lumens of the devices to be positioned at any appropriate location along the length of the main lumen and at any angle with respect to the longitudinal axis of the main lumen. Where there are two or more side branch lumens, the lumens may be spaced axially and circumferentially angled relative to each other to accommodate the target vasculature into which the implant is to be placed.

Still yet, the devices are constructed to have any suitable preformed shape, such as a curved tubular configuration, tapered or flared luminal ends and reduced or expanded central portions. Alternatively, the devices may have a naturally straight cylindrical configuration which is sufficiently flexible, both axially and radially, to accommodate the vasculature within which it is implanted. On the other hand, certain portions of the devices may be selected to have greater stiffness. As such, another aspect of the invention is to incorporate selective flexibility/stiffness into the device upon fabrication, where the gauge, thickness or width of the materials forming the lumens can be varied over the entirety of the device.

The subject devices may further include other materials which form at least a portion of the device, whether such portions may include the stent or the graft or all or portions of both. In certain embodiments, the graft is made from a biomaterial, such as an extracellular matrix, or other biodegradable material, which is coated or attached to at least a portion of the stent, whereby the material facilitates cellular integration of the device into the vessel wall.

The subject devices include additional features for improving and facilitating their delivery, deployment, positioning, placement, securement, retention and/or integration within the vasculature, as well as features which enable the devices to be removed or repositioned subsequent to at least partial deployment within the body.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Also for purposes of clarity, certain features of the invention may not be depicted in some of the drawings. Included in the drawings are the following figures:

FIGS. 11A-11G illustrate various steps in a method of fabricating a graft covering for a stent grafts of the present invention;

FIG. 12A illustrates a mandrel apparatus for forming convolutions in the graft covering of FIGS. 11A-11F; FIG. 12B is an enlarged cut-out view of a portion of the mandrel apparatus of FIG. 12A;

DETAILED DESCRIPTION OF THE INVENTION

Before the devices, systems and methods of the present invention are described, it is to be understood that this invention is not limited to particular therapeutic applications and implant sites described, as such may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The term "implant" or "implantable device" as used herein includes but is not limited to a device comprising a stent, a graft, a stent-graft or the like. The terms "proximal" and "distal" when used with reference to the implantable devices of the present invention, these terms are to be understood to indicate positions or locations relative to the intended implant site when it is operatively positioned therein. As such, proximal refers to a position or location closer to the origin or upstream side of blood flow, i.e., the closer to the heart, the more proximal the position. Likewise, distal refers to a position or location further away from the origin or closer to the downstream side of blood flow.

Referring now to the figures, the present invention will now be described in greater detail. It is noted that while each of the illustrated devices has a primary or main tubular member and at least one laterally extending tubular branch, the implantable devices of the present invention need not have side brandies.

Figure 1:
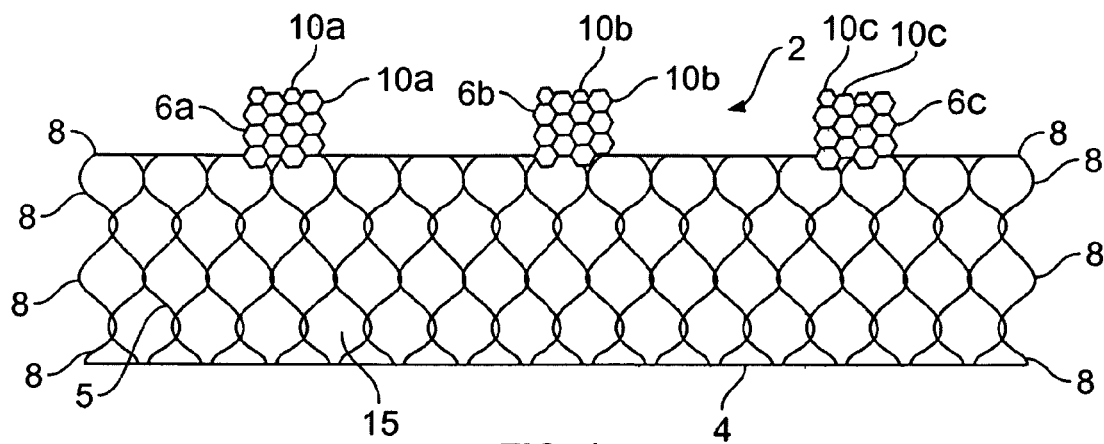
FIG. 1 illustrates an embodiment of a branched stent of the present invention in a natural, deployed state.

FIG. 1 illustrates one variation of an implantable device 2 having a primary tubular portion, body or member 4 and laterally extending side branches 6a, 6b and 6c, interconnected and in fluid communication with main body 4 by way of lateral openings within the body. The proximal and distal ends of the main tubular member 4 terminate in crowns or apexes 8, the number of which may vary. The distal ends of the side branches 6a, 6b and 6c terminate in crowns or apexes 10a, 10b and 10c, respectively, the number of which may also vary. Device 2 is particularly configured for implantation in the aortic arch where primary tubular member 4 is positionable within the arch walls and tubular branches 6a, 6b and 6c are positionable within the innominate artery, the left, common carotid artery and the left subclavian artery, respectively.

Figure 2:
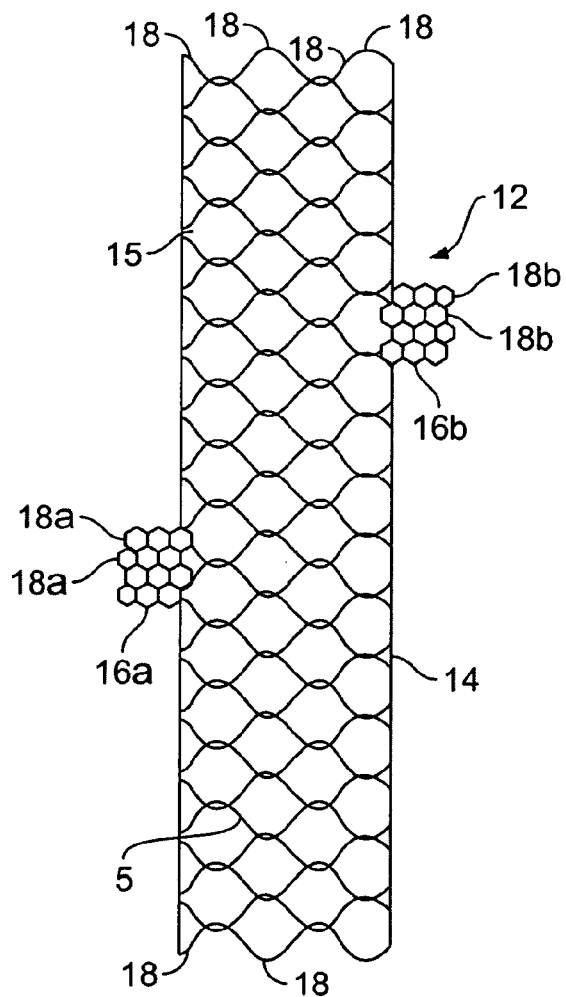
FIG. 2 illustrates another embodiment of a branched stent of the present invention in a natural, deployed state.

FIG. 2 illustrates another variation of a device 12 having a primary tubular portion or member 14 and laterally extending branches 16a and 16b, interconnected and in fluid communication with main body 14 by way of lateral openings within the body. The proximal and distal ends of the main tubular member 14 terminate in crowns or apexes 18 which are employed as described above with respect to FIG. 1 while the distal ends of the side branches 16a and 16b terminate in crowns or apexes 18a and 18b, respectively. Device 12 is particularly configured for implantation in the infra-renal aorta where primary tubular member 14 is positionable within the walls of the aorta and tubular branches 16a and 16b are positioned within the right and left renal arteries, respectively.

The subject devices are fabricated at least in part from one or more struts 5 which form interconnected cells 15. This construct enables the devices to be selectively manipulated to adjust at least a dimension (diameter and/or length), shape or orientation of the device. By "manipulated," it is meant that the device can be constrained, compressed, expanded, stretched, twisted, angled, etc. Whether any of these manipulations are necessary is at least partially dependent on the neutral or natural size of the stent lumens, the size of the vessels into which the lumens are to be implanted, the cross-sectional profile of the delivery system through which they are delivered to the implant site and the anatomy or spatial/dimensional configuration of the vessel into which the implant is to be positioned. For most endovascular applications, the lumenal diameters require reduction in order to fit within a delivery system, and then require subsequent reversal of the reduction to properly engage the vessel into which they are deployed. However, the lumen diameters, once deployed within the vasculature, may not necessarily fully expand to their natural/neutral size as they will be constrained by the vasculature. In some instances, the stent lumens may require expansion subsequent to deployment within the vasculature in order to adequately engage the vessel walls.

Generally, the devices of the present invention have a first, unreduced or neutral dimension "X" and a second or reduced dimension "Y" which is anywhere from one half or less to one tenth or less of the first dimension "X." Such a dimension is often a diameter or length of the device where the diameter or length of at least the main lumen of the stent, and most typically of all of the side branch lumens as well, can be changed or moderated between X and Y.

Typically, the subject devices for most vascular applications will have a main branch lumen having an unconstrained length in the range from about 1 cm to about 25 cm and an unconstrained diameter in the range from about 2 mm to about 42 mm; and side branch lumens having an unconstrained length in the range from about 0.5 cm to about 8 cm and an unconstrained diameter in the range from about 2 mm to about 14 mm. For aortic applications, the unconstrained length of the main lumen is typically from about 8 cm to about 25 cm and the unconstrained diameter is in the range from about 15 mm to about 42 mm; and the side branch lumens will have an unconstrained length in the range from about 2 cm to about 8 cm and an unconstrained diameter in the range from about 5 mm to about 14 mm. Where the dimension is the diameter of the main lumen of the stent, the reduced diameter is more likely to be closer to one tenth of the unreduced diameter. For renal applications, the main branch lumen will have an unconstrained length in the range from about 2 cm to about 20 cm and an unconstrained diameter in the range from about 12 mm to about 25 mm; and the side branch lumens will have an unconstrained length in the range from about 0.5 cm to about 5 cm and an unconstrained diameter in the range from about 4 mm to about 12 mm. For coronary applications, the main branch lumen will have an unconstrained length in the range from about 1 cm to about 3 cm and an unconstrained diameter from about 2 mm to about 5 mm; and the side branch lumens will have an unconstrained length in the range from about 0.5 cm to about 3 cm and an unconstrained diameter in the range from about 2 mm to about 5 mm. For applications in smaller vessels, such as the neurovasculature, these dimensions will of course be smaller. In certain applications, particularly where treating a vascular aneurysm having a relatively large neck section located near a juncture between the main vessel and a tributary vessel, it may be preferential to provide a branched stent where the side branch lumens are relatively longer than average. The lengthier stent branches can bridge the neck opening while maintaining sufficient length at their distal ends to extend a distance into a vascular side branch sufficient to anchor the stent.

Adjustability in the length and/or diameter of the main lumen as well as the length and/or diameter of the side branch lumens of the devices enables them to accommodate curvaceous or tortuous vasculature encountered along the delivery path and at the implant site. In one aspect, the diameters of the device lumens may be compressed to enable the device to fit within a smaller-diameter delivery sheath or catheter, yet they may also be expandable beyond a natural or neutral diameter to engage the vasculature wall at the implant site. In many embodiments, changing the diameter or length of a lumen results in a corresponding change in the other dimension. More specifically, compressing a lumen's diameter will increase its length, and expanding a lumen's diameter may result in foreshortening of the lumen's length.

Figure 3A:
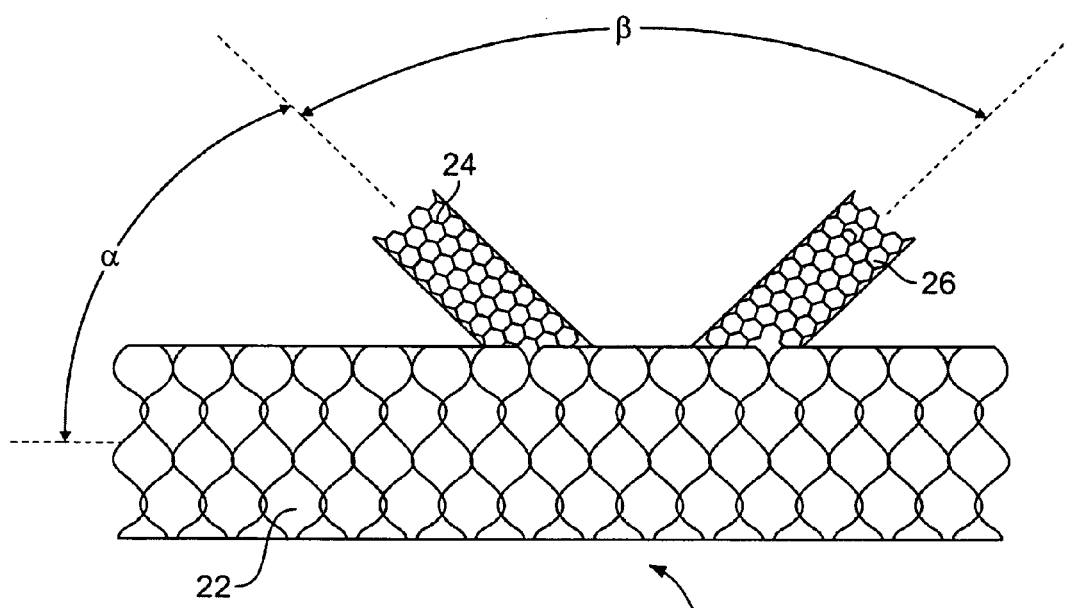
FIG. 3A illustrates another embodiment of a branched stent in which the side branch lumens are angled.
Figure 3B:
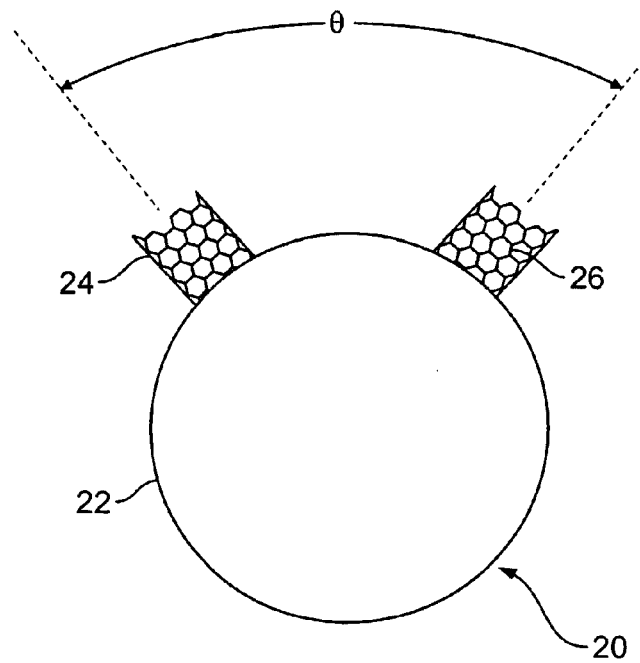
FIG. 3B illustrates an end view of the stent of FIG. 3A.

In another aspect, the orientation of a side branch with respect to the main branch may be adjustable within a certain range. In particular, the side branches are rotationally adjustable relative to the main lumen, i.e., the angle at which each of the side branches intersects the main lumen may be varied. FIG. 3A illustrates an implant device 20 in which side branch lumens 24 and 26 each has an angular orientation, defined by angle α, with respect to main lumen 22, and has an angular orientation, defined by angle β with respect to each other. FIG. 3B is an end view of implant device 20 which illustrates the circumferential orientation, defined by angle θ, between side branch lumens 22 and 24. Typical ranges of the various angles are as follows: from about 10° to about 170° for angle α, from 0° to about 170° for angle β, and from 0° to 360° for angle θ.

Each of a stent's branched lumens has a naturally biased orientation in an unconstrained, pre-deployed condition, i.e., the neutral state. This orientation range is built into the device upon fabrication and is selected to accommodate any possible variation in the anatomy being treated. One or more of the branched lumens may be selectively adjusted within the orientation range upon delivery and placement of the branch lumens within the respective vessel lumens. For example, the stent may be fabricated with one or more side branches having neutral orientations at substantially right-angles with respect to axis of the main lumen, which natural orientation may be adjusted in any direction to accommodate the orientation of side branch vessel at the implant site into which the stent is placed. Such angular orientation of the side branch lumens with respect to the main lumen may be axial, circumferential or both. Where two or more side branches are employed on a subject device, the linear distance between the side branches may also be varied by selective stretching or foreshortening of the stent material positioned between the side branches. In this way, the subject invention is able to address patient-to-patient anatomical inconsistencies with only a single-sized device. In one application, the devices are constructed to accommodate the variability in spacing between or the angular orientation of the tributary vessels of the aortic arch.

The shape of the implant's lumens may also vary or be adjusted as needed to accommodate the vessel into which it is positioned. Each of a device's lumens may have a natural, preformed shaped, e.g. curved, that accommodates the shape of the vessel into which it is to be placed. Alternatively, the lumens may be made with a neutrally straight configuration but are flexible enough to accommodate the natural curvature of the vessel into which they are implanted.

The subject devices may also be fabricated such that, their lumens may have constant or variable stiffness/flexibility along their lengths as well as about their circumferences. Greater flexibility can better accommodate curvaceous vasculature encountered during delivery and at the implant site. Such a feature is highly beneficial in aortic arch stenting applications due to the relatively "tight" curve of the arch. Enhanced stiffness, on the other hand, particularly at the end portions of a lumen, imparts a greater radial force thereby resisting migration of the device within the vasculature after placement. Variable flexibility/stiffness may be implemented in a variety of ways.

The gauge or thickness of the strut or starts (i.e., the elemental portions that form a stent cell) used to fabricate the devices may vary where thicker gauges impart greater stiffness and thinner gauges impart greater flexibility. The struts of a stent may vary in diameter (in wire embodiments) or thickness or width (in sheet and cut tube embodiments). In one variation, a single wire or filament may be used where the gauge selectively varies along its length. The thicker gauge portions are used to form at least the end portions of the stent lumen(s) to increase their radial force thereby reducing the risk of stent migration. Conversely, the narrower gauge portion(s) of the wire form at least a central portion of the main stent lumen (and may also form portions of the side branch lumens) which may be relatively more flexible than the end portions to facilitate delivery of the stent within tortuous or curving vasculature or enabling the device to be compact into the delivery sheath more easily.

In other embodiments, more than one wire is used where the wires each have constant gauges along their respective lengths but differ from wire to wire. Larger gauge wire(s)

may be used to form the stent ends or other areas where increased stiffness is required while narrower gauge wire(s) may be used to form other portions, e.g., the central portions of the stent lumens, where increased flexibility is required or the cells of the side branch stents where decreased radial force is required relative to the radial force required for the main body portion. Additionally or alternatively, the larger gauge wire can be selectively doubled-over or wrapped with the narrow gauge wire at selected points or locations about the stent to bolster the stiffness at those particular sites.

In one variation, two or more wires may be employed to form the device whereby the wire ends, i.e., four wire ends in the case of a device made from two wires, are joined together. The location(s) about the lumens at which the wires cross-each and/or at which their ends are joined about is/are selected to minimize stiffness in certain areas along or about the lumen and/or to enhance stiffness in one or more other areas of the device, i.e., to provide relative stiffness and flexibility between portions of the stent. For example, in aortic arch applications, the portion of the main lumen of the stent intended to be aligned along the inferior wall of the arch is preferentially relatively more flexible and/or less stiff than the portion of the stent intended to be aligned along the superior wall of the arch, as the inferior wall has a tighter radius of curvature. Accordingly, it may be desirable to minimize the joinder and/or intersection points of the wires along this portion of the stent.

Figure 4:
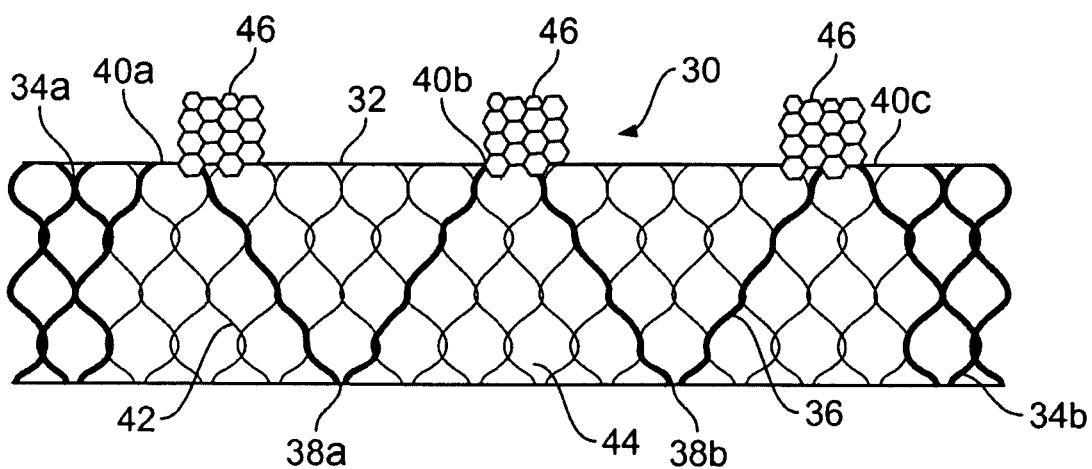
FIG. 4 shows an embodiment of a branched stent fabricated from wire having more than one gauge.
Figure 5:
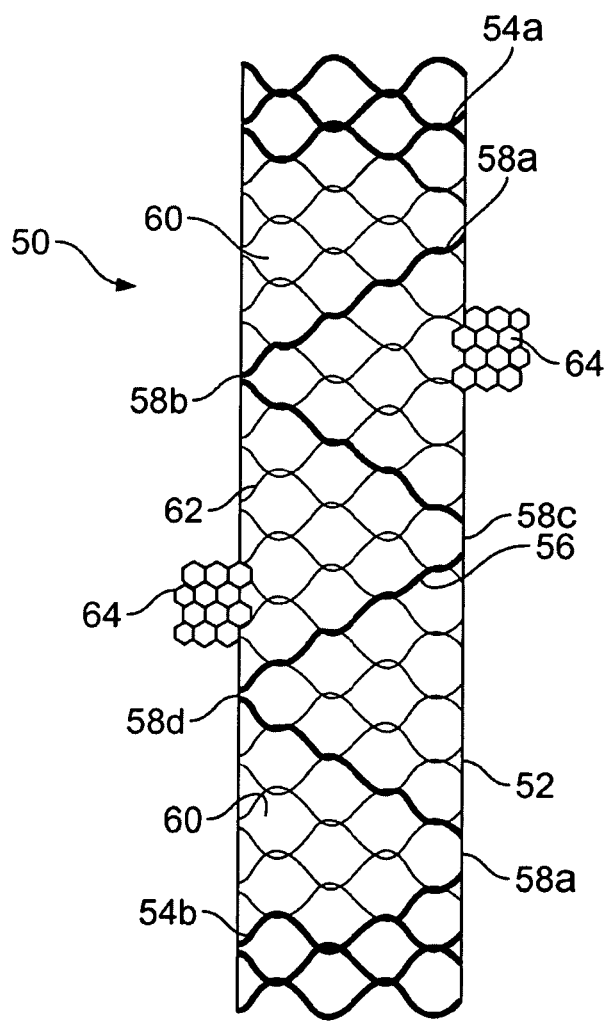
FIG. 5 shows another embodiment of a branched stent fabricated from wire having more than one gauge.
Figure 6:
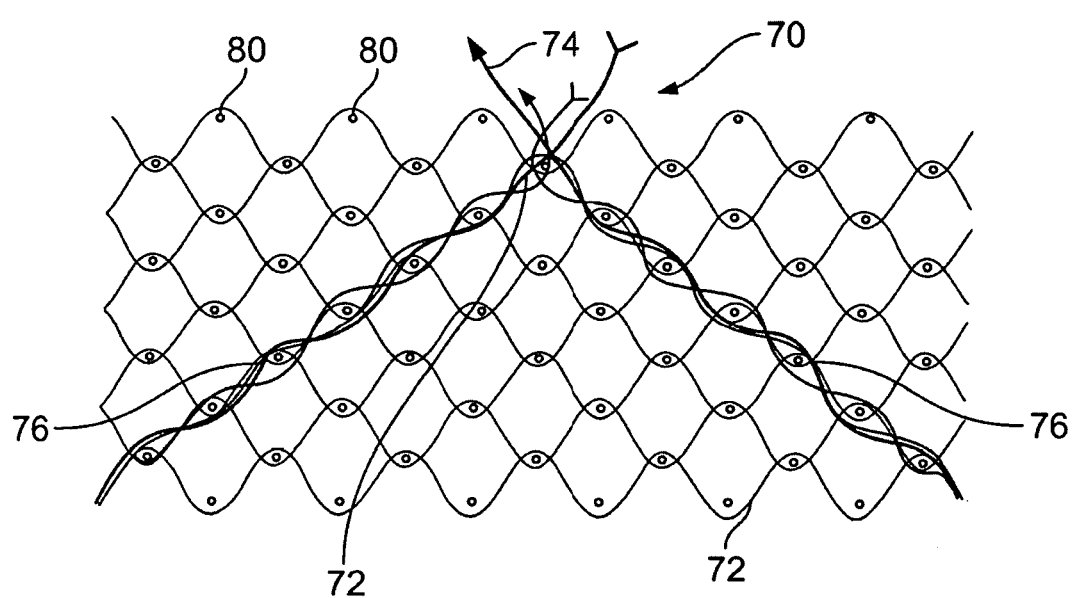
FIG. 6 illustrates an enlargement of a portion of a stent body fabricated from wire having more than one gauge.

FIGS. 4-6 illustrate embodiments of the subject devices which employ varying gauges of wire. The main tube 32 of device 30 of FIG. 4 is fabricated from at least two gauges of wire (either one wire having at least two gauges or two or more wires having different gauges) where a heavier gauge 36 is used to fabricate end portions 34a and 34b and a thinner gauge 42 is used to fabricate other portions 44 therebetween. A thicker gauge wire 36 is also selectively weaved or threaded throughout main tube 32. For example, wire(s) 36 is/are used at the junctures 40a, 40b, 40c between the side branch lumens 46 and main lumen 32. While providing stability at the junctures, the heavier gauge wire does not impede a side branch stent's flexibility to fold against the main lumen for purposes of delivery through a sheath. Additionally, the thicker wire 36 may be crossed-over on itself or, where two or more wires are used, the wires may be caused to intersect at other locations 38a, 38b where additional stiffness is desired. Here, the portions of the main stent lumen directly between (and on the same side as) the side branch lumens 40a, 40b, 40c are free of the thicker gauge wire. Minimizing the wire gauge at these locations increases flexibility and the ability to adjust (stretch or compress) the linear distance between the side branches, a feature quite often needed for aortic arch applications Main lumen 52 of device 50 of FIG. 5 is fabricated in a similar manner with end portions 54a, 54b having a thicker gauge wire 56 and more centrally located portions 60 having a narrow gauge wire 62. Unlike device 30, the junctures between the side branch lumens 64 and the main lumen 52 are not reinforced with the thicker gauge wire. Here, also, both sides of main lumen 52 are somewhat equally reinforced (at locations 58a-58e) to impart substantially equal flexibility/stiffness on both sides of the device 50.

FIG. 6 shows an enlarged portion 70 of a device of the present invention fabricated from two wires, one having a thinner gauge 72 and the other having a thicker gauge 74. The thinner gauge wire 72 is used to fabricate the majority of the stent body which is reinforced in certain areas by the thicker gauge wire 74. As mentioned above, the reinforcement can be accomplished by weaving together two or more lengths of the thinner gauge wire 72 and/or by weaving the thicker gauge wire 74 along a weave pattern or line of thinner gauge wire, as referenced by 76 in the figure. Alternatively or additionally, the wires may be intersected at certain selected points 78 about the area of the stent body to increase stiffness at those points.

The devices of the present invention are additionally advantageous in that they are self-securing to prevent migration within the vasculature. Such a feature may be implemented in a variety of different ways. First, the device lumens may be constructed having ends (for both main and side branches) which have expanded or flared diameters that place sufficient radial force on the interior wall of the vessel into which they are implanted to resist against intravascular pressures. As mentioned above, thicker gauge wire at the end portions of the device may provide additional radial force. Additionally or alternatively, the number of apices at the stent ends may be increased as needed to increase the radial force at the end portions. Typically, at least three apices are employed at each of the lumenal ends (main lumen and side branch lumens), where larger lumens require more apices to maintain the desire radially force to be placed on the vessel wall. In branched devices, migration prevention may be addressed by integrating the cells of a side branch lumen with the cells of the main body lumen. More specifically, the interconnection of the side branch lumen to the main body lumen is accomplished by forming the side branch lumen and the main body lumen from the same wire or filament. Thus, when the side branch is deployed within and held in place by the side branch artery, the main body of the stent cannot migrate. Such "passive" anchoring mechanisms are atraumatic, as opposed to an active anchoring means, such as barbs or hooks, which may damage the cellular structures of the implant site leading to smooth muscle proliferation, restenosis, and other vascular complications such as perforations, tearing or erosion.

As mentioned above, the implantable devices of the present invention may include a stent or a graft or a combination of the two, referred to as a stent graft, a stented graft or a grafted stent. The stents and grafts of the present invention may be made of any suitable materials known in the art. Preferably, the stent cell structure is constructed of wire, although any suitable material may be substituted. The wire stent should be elastically compliant, for example, the stent may be made of stainless steel, elgiloy, tungsten, platinum or NITINOL but any other suitable materials may be used instead of or in addition to these commonly used materials. The entire stent structure may be fabricated from one or more wires woven into a pattern of interconnected cells forming, for example, the closed chain link configuration illustrated in FIG. 6.

Figure 10A:
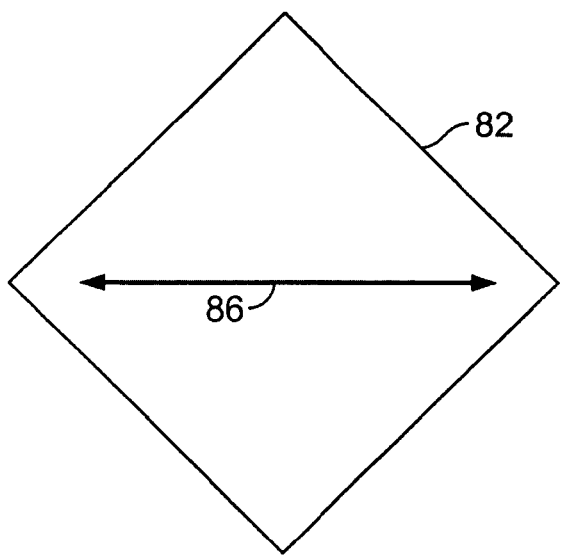
FIGS. 10A and 10B are schematic illustrations of single stent cells.
Figure 10B:
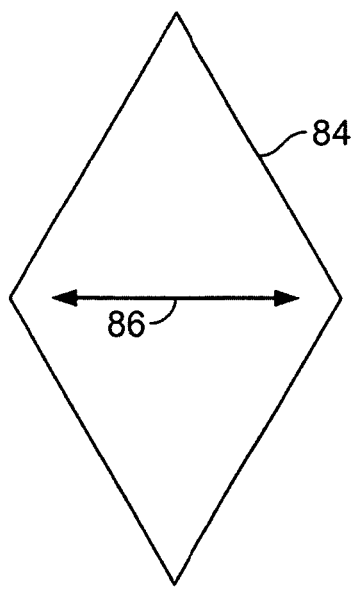

The stent structure may have asymmetrical cell sizes, e.g., cell size may vary along the length or about the circumference of the stent. For example, in one variation, as illustrated in FIGS. 10A and 10B, a subject stent has a first or larger cell size 82 at one or more sections of its lengths and has a second or smaller cell size 84 at one or more other sections of its length. Here "cell size" is referring to the dimension of the cell along the longitudinal direction 86 of the stent. The smaller or narrow cells 84 provide greater radial force to the stent as well as better conformability to curved vascular geometry. As such, the length portions at the ends of the main stent lumen and at selected central portions of the main lumen that may be subject to particularly curved vasculature. For example, in aortic arch applications, smaller cell sizes at the length portion(s) extending between the side branch stent lumens may be beneficial as the portions, after implantation of the stent, are positioned at the apex of the curve or at the sharpest curvature of the arch, particularly at the inside curve (lower arch curve). With smaller cells, the likelihood of the cell struts extending into the stent lumen is minimized. In other stent variations, the cell size of the side branch lumens is gradually reduced in the distal direction. This facilitates the ability to selectively stretch the distal most portion of the side branch lumens and, thus, makes it easier for a physician to guide the distal end of the side branch into a designated vessel.

Figure 7A:
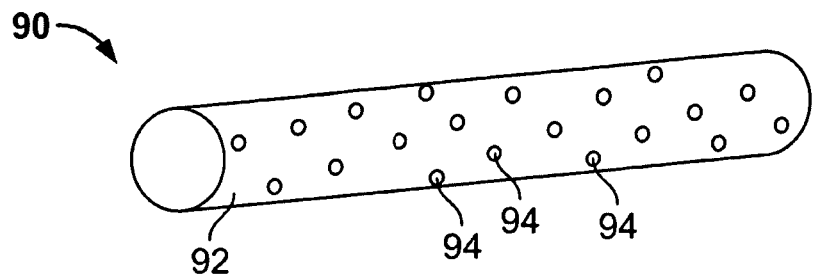
FIGS. 7A-7C illustrate various exemplary mandrel designs for fabricating the stents and stent grafts of the present invention.
Figure 7B:
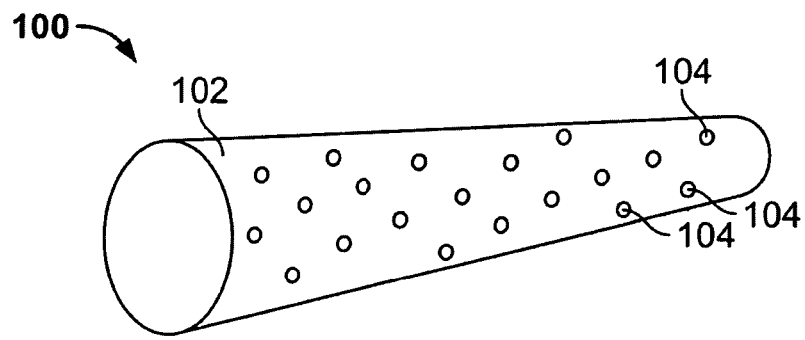
Figure 7C:
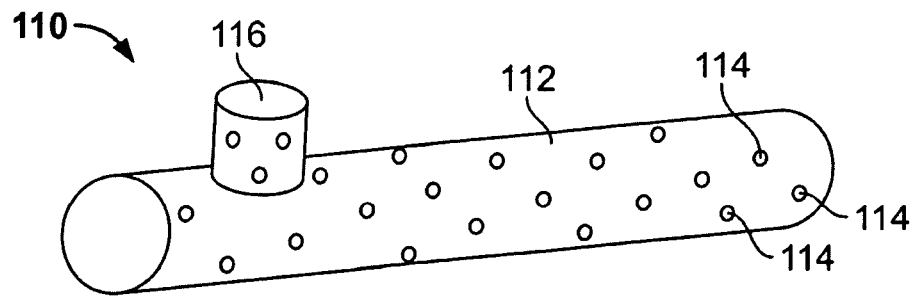

The wire-formed stents of the present invention may be fabricated in many ways. One method of making the wire stent is by use of a mandrel device such as the mandrel devices 90, 100 and 110 illustrated in FIGS. 7A-7C, respectively. Each of the devices has at least a main mandrel component 92, 102, and 112, respectively, with a plurality of selectively positioned pinholes 94, 104 and 114, respectively, within which a plurality of pins (not shown) are selectively positioned, or from which a plurality of pins is caused to extend. As is described in more detail below, the stent structure is formed by selectively wrapping a wire around the pins. Where the stent is to have one or more side branch lumens, the mandrel device, such as device 110 of FIG. 7C, may be provided with at least one side mandrel 116 extending substantially transverse to the main mandrel 112, where the number of side mandrels preferably corresponds to the number of stent side branches to be formed. The mandrel devices may be modular where side branch mandrels of varying diameters and lengths can be detachably assembled to the main mandrel. The configuration of the main mandrel as well as the side branch mandrel(s) may have any suitable shape, size, length, diameter, etc, to form the desired stent configuration. Commonly, the mandrel components have a straight cylindrical configuration (see FIGS. 7A and 7C) having a uniform cross-section, but may be conical with varying diameters along a length dimension (see FIG. 7B), frustum conical, have an oval cross-section, a curved shape, etc.

The pins may be retractable within the mandrel components or are themselves removable from and selectively positionable within holes formed in the mandrel components. Still yet, the mandrel device may be configured to selectively extend and retract the pins. The number of pins and the distance and spacing between them may be varied to provide a customized pin configuration. This customization enables the fabrication of stents having varying sizes, lengths, cell sizes, etc. using a limited number of mandrel components. For example, in one variation, the pins are arranged about the mandrel components in an alternating pattern such as for example, where about 50% of the pinholes per row will be filled with pins. Alternatively, a selection of mandrels may be provided, each having a unique pinhole pattern which in turn defines a unique stent cell pattern.

To form the stent, a shape memory wire, such as a NITINOL wire, having a selected length and diameter are provided. Typically, the length of the wire ranges from about 1 foot (in the case of a short "cuff" extender) to about 12 feet long, but may be longer if needed or shorter if more practical, depending on the desired length and diameter of the stent to be formed. The wire's diameter is typically in the range from about 0.001 to about 0.020 inch. After providing a mandrel device having winding pins at the desired points or locations on the mandrel components, the wire is wound about the pins in a selected direction and in a selected over-and-under lapping pattern, e.g., a zigzag pattern, to form a series of interconnected undulated rings resulting in a desired cell pattern.

An exemplary wire winding pattern is illustrated in FIG. 6. Starting from one end of the main mandrel, the wire 72 is wound around the pins 80 in a zigzag pattern back and forth from one end of the main mandrel to the other until the cells of the main lumen of the stent have been formed. Next, the same or a different wire is used to form the side branch lumen(s) where the wire is wrapped in a zigzag fashion from the base of the side branch mandrel to the distally extending end and back again until all of the cells of the side branch have been created. Then the wire is wound about the main mandrel along a path that is at an angle to longitudinal axis of the main mandrel where the wire is doubled over itself along certain cell segments, as indicated by reference number 76. It should be noted that any lumen of the stent may be fabricated first, followed by the others, or the winding pattern may be such that portions of the various lumens are formed intermittently.

The mandrel device with the formed wire stent pattern are then heated to a temperature in the range from about 480° C. to about 520° C. and typically to about 490° for approximately 20 minutes in a gaseous environment, however, this time may be reduced by using a salt bath. The duration of the heat-setting step is dependent upon the time necessary to shift the wire material from a Martensitic to an Austenitic phase. The assembly is then air cooled or placed into a liquid quench bath (which can be water or other suitable liquid) for 30 seconds or more and then allowed to air dry. Once the stent is sufficiently dried, the pins are either pulled from the mandrel device or retracted into the hollow center of the mandrel by an actuation of an inner piece which projects the pins out their respective holes in the outer surface of the mandrel. Once the side branch mandrels are removed, the stent, with its interconnected lumens, can then be removed from the mandrel device. Alternatively, with the mandrel components detached from one another, one of the lumens, e.g., the main stent lumen, may be formed first followed by formation of a side branch lumen by attachment of a side mandrel to the main mandrel.

As discussed above, selected regions of the stent may be fabricated from wire selectively reduced in diameter. The selective diameter reduction may be accomplished by selectively etching or e-polishing the certain stent struts located at the portions of the stent where less stiffness and a reduced radial force are desired. This can be done by selective immersion of the side branch in an acid during manufacture to reduce the amount of metal in a particular region of the stent. Another method to accomplish the desired result of preferentially reducing side branch longitudinal stiffness and/or outward radial force of the side branch component is to use an electropolishing apparatus. By placing the woven solid wire stent into an electrolyte bath and applying a voltage potential across an anode-cathode gap, where the stent itself is the anode, metal ions are dissolved into the electrolytic solution. Alternatively, or subsequently, the process may be reversed wherein the stent becomes the cathode and the side branch or other selected region of the stent may be electroplated with a similar or different metal in ionic solution, for instance gold or platinum, in order to either change the mechanical properties or to enhance the radiopacity of the selected region. Those skilled in the art of electroplating and electropolishing will recognize that there are techniques using a "strike" layer of a similar material to the substrate in order to enhance the bonding of a dissimilar material to the substrate. An example would be the use of a pure nickel strike layer on top of a NITINOL substrate in order to subsequently bond a gold or platinum coating to the substrate.

Another method of making the stent is to cut a thin-walled tubular member from a tube or flat sheet of material by removing portions of the tubing or sheet in the desired pattern for the stent, leaving relatively untouched the portions of the metallic tubing which are to form the stent. The sheet material may be made of stainless steel or other metal alloys such as tantalum, nickel-titanium, cobalt-chromium, titanium, shape memory and superelastic alloys, and the nobel metals such as gold or platinum.

In addition to these methods, other techniques known to one of skill in the art may be employed to make the subject stents. Some of these methods include laser cutting, chemical etching, electric discharge machining, etc.

Figure 8:
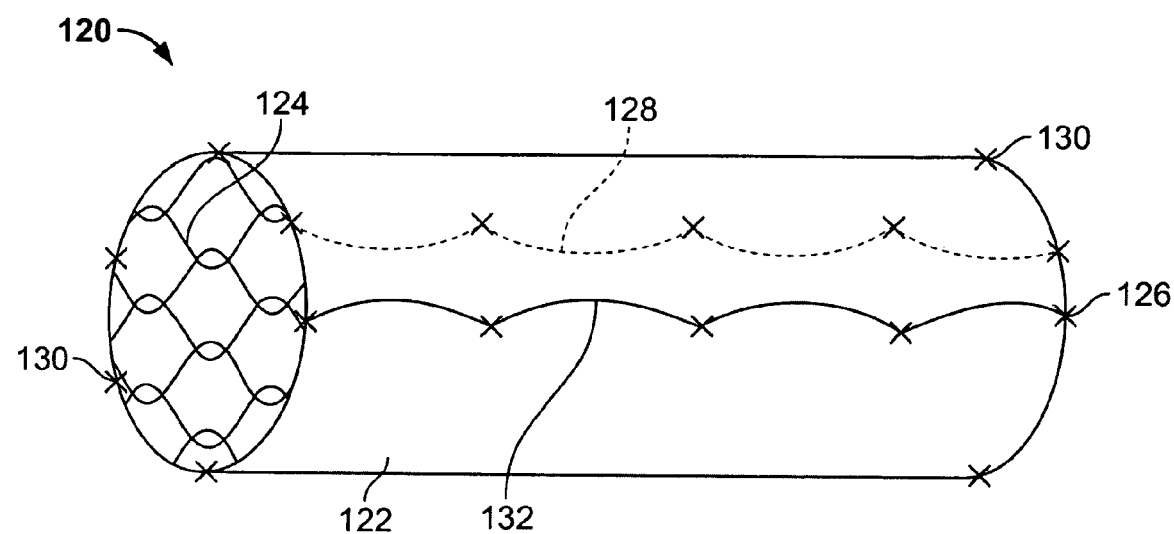
FIG. 8 illustrates one manner in grafting a stent of the present invention.

Referring now to FIG. 8, where a stent graft 120 is to be formed by the addition of a graft material 122, such as an ECM material, to the subject stent 124, any manner of attaching the graft material to the wire form may be used. In one variation, the graft material is attached by way of a suture 126. As such, one edge 128 of the graft material is stitched lengthwise to the stent frame 124 along the stents length, where at least one knot 130 is tied at each apex of the stent to secure an end of the graft to the stent. Then the graft material 122 is stretched around the surface of the stent and the opposite edge 132 of the graft is overlapped with the already attached edge 128 and independently stitched to the stent frame to provide a leak free surface against which blood cannot escape. The graft material is stretched to an extent to match the compliance of the stent so that it does not drape when the stent is in the expanded state. Upon complete attachment of the graft material to the stent, the graft is dehydrated so that it snuggly shrinks onto the stent frame similar to heat shrink tubing would when heated.

Figure 11A:
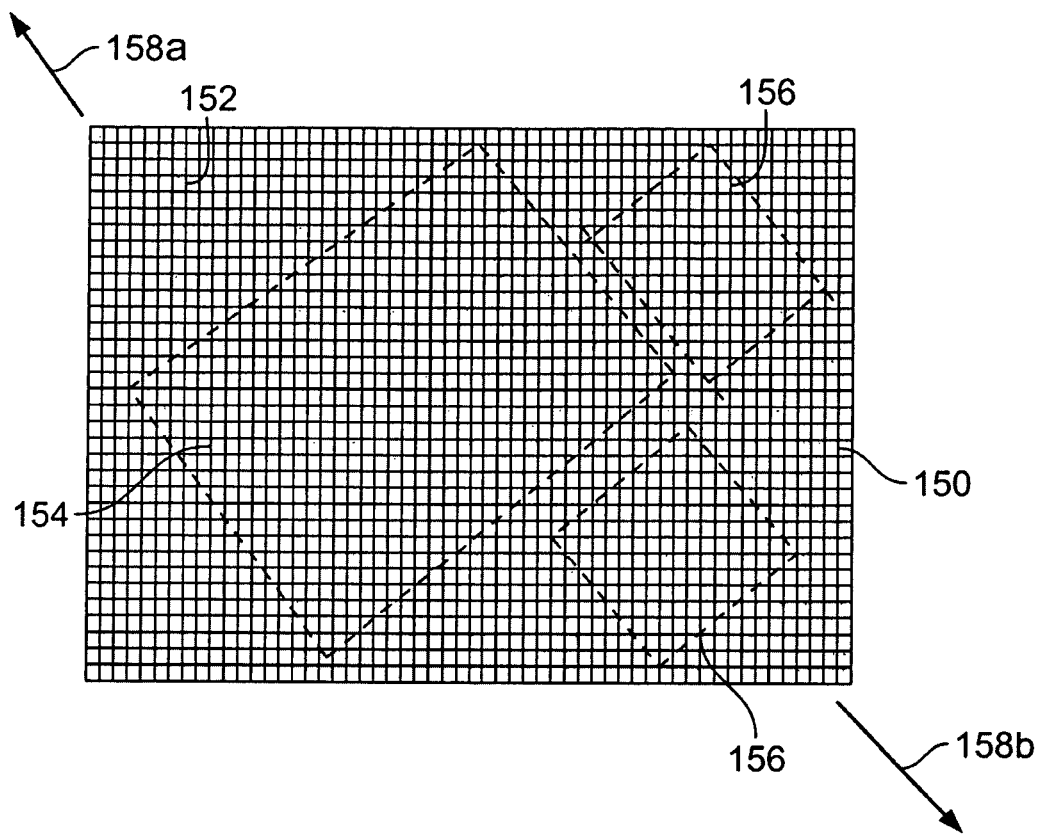
Figure 11B:
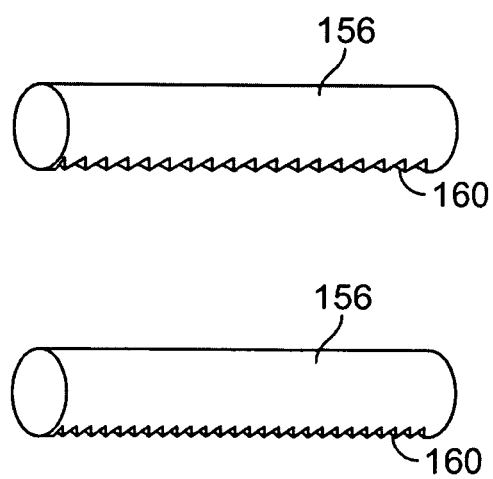
Figure 11C:
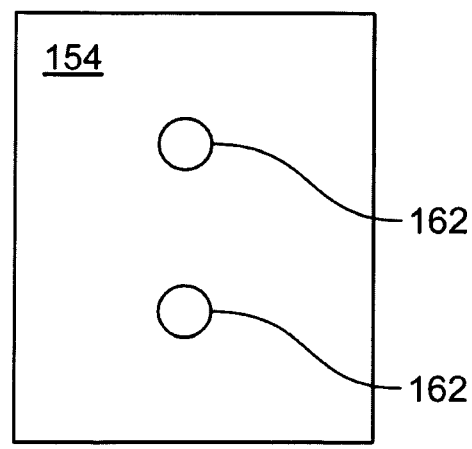
Figure 11D:
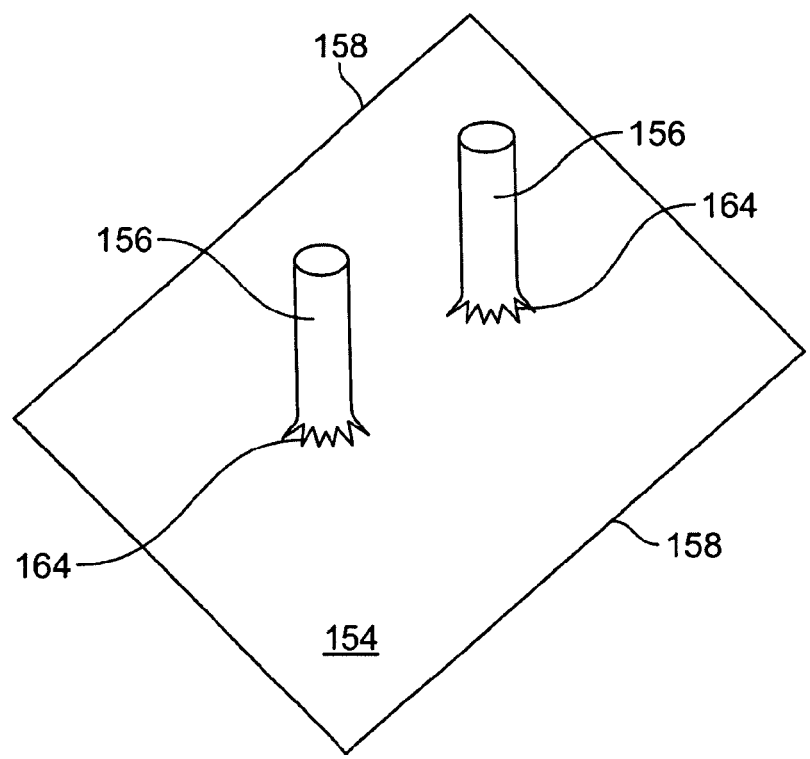
Figure 11E:
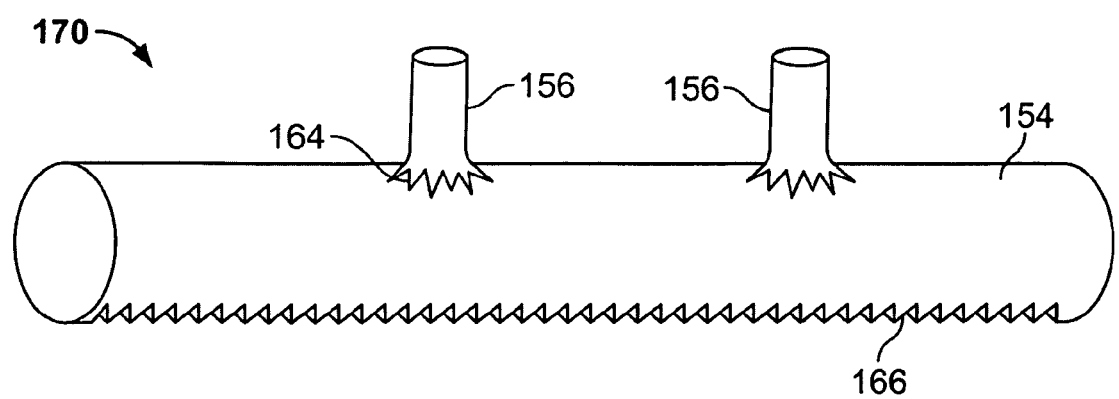
Figure 13A:
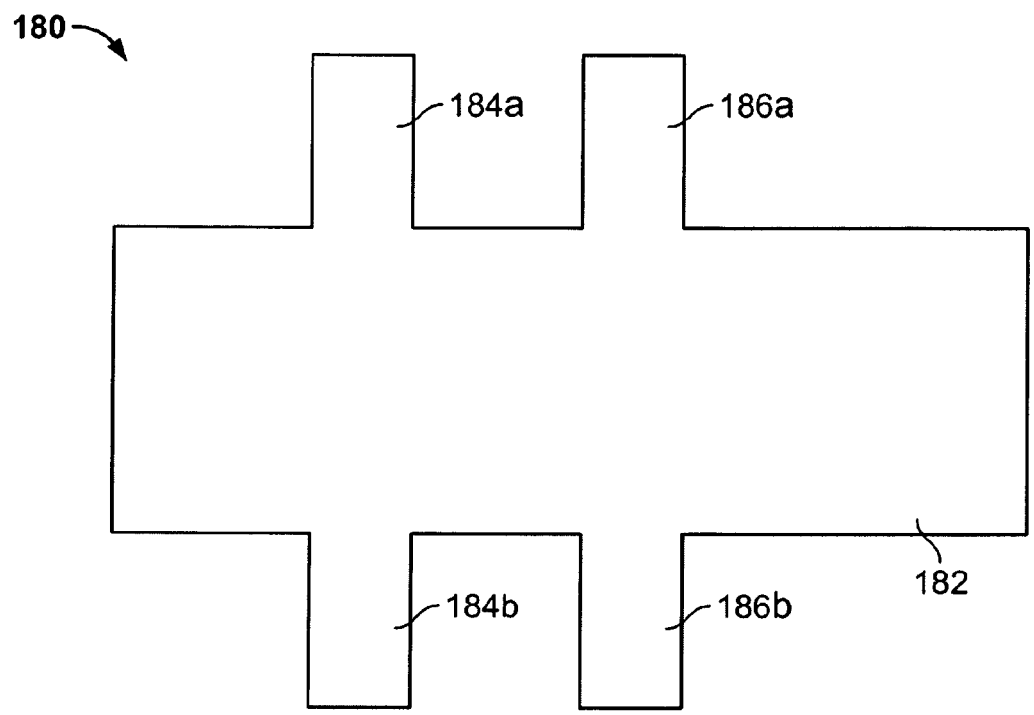
FIGS. 13A-13C illustrate various steps in another method of fabricating a graft covering for a stent grafts of the present invention.
Figure 13B:
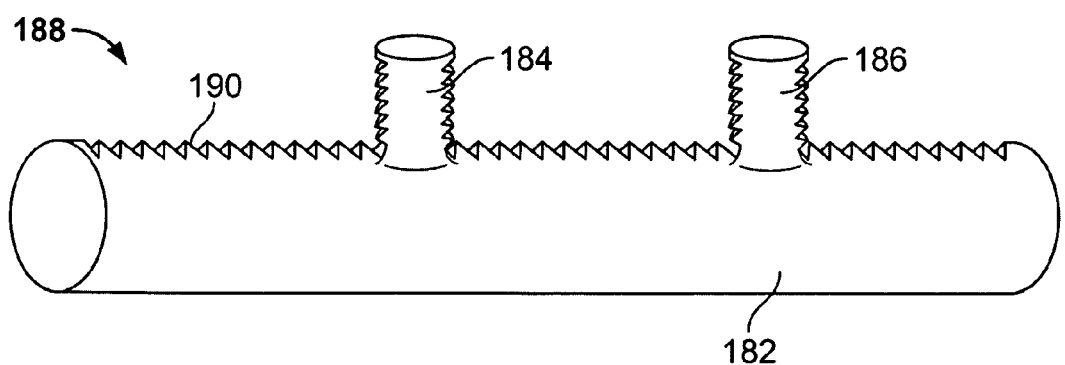
Figure 13C:
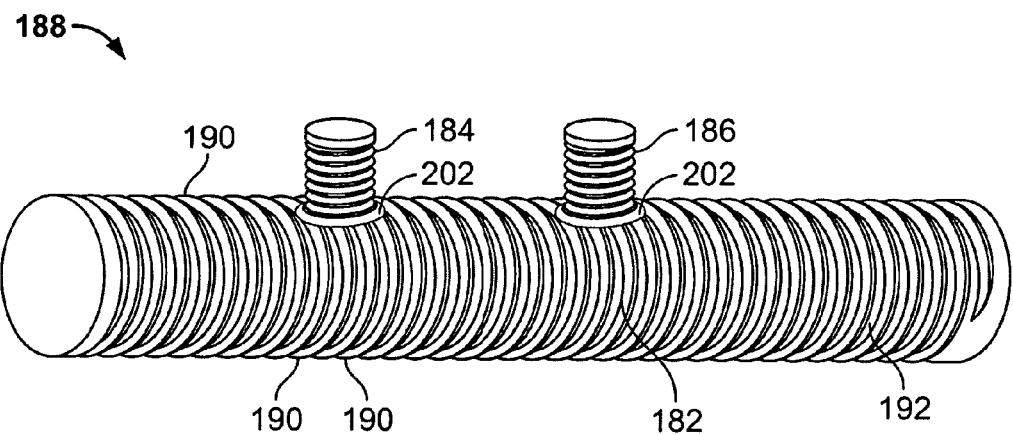

FIGS. 11A-11F illustrate a method of fabricating a stent graft of the present invention from a woven or knitted-type graft fabric, such as polyester. As shown in FIG. 11A, a sheet 150 of the material or fabric is provided and preferably stretched in a direction 158a, 158b diagonal to the natural weave 152 of the material (shown boldly and in exaggerated size in FIG. 11A for illustration purposes only). While the sheet is stretched, pieces or swatches of the material are cut from the sheet where the swatches have length and width dimensions corresponding to the length and circumference dimensions of the main lumen 154 and side branch lumens 156 of the stent graft to be formed. As illustrated in FIG. 11A, the material is preferably cut at an angle or diagonal to the weave pattern 152 the swatches that forms the material. The stretch undergone by the material remains fixed with the resulting orientation of the pre-stretched weave pattern enabling the resulting grafts to be highly stretchable when stretched along an axis perpendicular (or opposite) to the direction of pre-stretch undergone by the material. Next, each of the side branch swatches 156 is folded to coapt opposing side edges of the material (not shown) which are then sutured together to form a side branch graft, as shown in FIG. 11B. The sutures may be formed in a "Z" stitch pattern 160 (commonly known to those skilled in art) to further enhance the stretchability of the juncture between the pieces of fabricated. The suture material may be made of radiopaque material for imaging the stent graft during the implantation procedure. As shown in FIG. 11C, holes 162 are cut or punctured into the main lumen swatch 154 corresponding to the number and location of the side branch stent graft lumens 156. The edges of the holes may be fused or otherwise treated to prevent fraying of the material. As shown in FIG. 11D, the side branch grafts 156 are then sutured to swatch 154 at holes 162 using the same "Z" stitch pattern 164. Swatch 154 is then folded to coapt its longitudinal edges 158 which are sutured together using the same stitch pattern 166 to form the main lumen graft. It may be particularly beneficial to employ a radiopaque suture for stitching 166 to define a longitudinal marking on the stent graft for facilitating proper alignment of the stent graft, at a vascular implant site. The collectively assembled and attached fabric lumens form a branched graft 170 (FIG. 11E) for covering a branched stent of the present invention.

While the pre-stretched graft lumens provide suitable stretchability for covering a stent and also enhance the flexibility and adjustability of the resulting stent grail, as described above, "convoluting" the graft lumens may provide even further enhancement of these features. By "convoluting", it is meant that preformed ridges and grooves are formed within the graft material about the graft's circumference (FIG. 11F), i.e., a wave pattern 175a is formed along the graft's length, as best illustrated by the schematic cross-sectional cut-out view in FIG. 11G. The convolutions may be formed in the graft material either prior to after forming the graft's tubular lumens. A technique for forming the convolutions subsequent to forming the tubular structures is described below, however, those skilled in the art will appreciate and understand that such convolutions may be formed while the graft material is still in the planar form.

FIG. 12A illustrates a mandrel device 180 which may be used to form the convolutions within the graft, material, however, any suitable means and method may be employed. Mandrel apparatus 180 has a main mandrel 182 sized for insertion within main lumen 154 of graft 170 and includes any number of secondary mandrel components 184 size for insertion into the respective side branch graft lumens 156. A plurality of threaded bore holes 192 extend radially within main mandrel 182 for receiving and securing to the distal threaded ends 190 of the respective side or secondary mandrels 184. The selection of space apart bore holes 192 allows mandrel device 180 to be used to convolute grafts having any number and spacing of side grafts. While not illustrated, bore holes may be provided laterally of each other and/or on opposing sides of main mandrel 180 to accommodate any configuration of stent, such as those illustrated in FIGS. 1, 2 and 3. The surface of each mandrel component has one or more sections 186, 188 within which a convolution pattern 175b has been formed. While the convolution pattern 175b, best illustrated by the schematic cross-sectional cut-out in FIG. 12B, is shown having a square wave pattern, any repetitive pattern (e.g., sine wave) may be employed.

Fabricating the convolutions within graft 170 involves first inserting main mandrel component 182 within graft 170 and positioning the graft over the mandrel's convolutions 175b. Threaded boreholes 192 within the surface of mandrel 182 are then aligned with side branch lumens 156 of graft 170 to allow for axial passage of the distal ends 190 of side mandrels 184 through the side branch lumens 156 into bore holes 192. The graft material is then heat-set over mandrel device 180 whereby the fabric is caused to shrink and tighten around convolution pattern 175b. Heat setting may be accomplished by placing the mandrel fitted with the graft into an oven or by using a heat-emitting device where the heat-setting can be focused and targeted. The heat-setting causes the convolution pattern 175a to be formed within graft 170, as illustrated in FIGS. 11F and 11G. Once the pattern is set, the mandrels 182, 184 are removed from the graft lumens. It is noted that the convolutions may be formed in each of the main graft and side branch grafts prior to attaching the grafts to each other by using each of the aforementioned mandrel components individually.

Optionally, another radiopaque stitching pattern 176 (shown in FIG. 11F) may be made within graft 170, running longitudinally along the main lumen 154 and positioned approximately 180° about the circumference from stitching pattern 166. The additional stitching pattern further facilitates image-guided delivery and proper alignment of the stent graft at an implant site. One or more corresponding radiopaque markings may also be provided within the stent delivery sheath whereby the radiopaque markings on the stent graft are aligned with those on the delivery sheath to ensure proper orientation of the stent graft within the sheath, as well as to facilitate proper alignment of the delivery sheath during the implant procedure.

Referring now to FIGS. 13A-13D, another graft fabrication method is described. Using the stretching and cutting techniques described above with respect to FIG. 11A, a single swatch 180 is formed having a cross pattern or the like whereby an elongated rectangular section 182 defines the main graft lumen to be formed and one or more smaller and shorter rectangular sections 184, 186 intersecting main section 182 define the side branch graft lumens to be formed. Swatch 180 is then folded lengthwise along section 182 such that the opposite edges of the material are apposed with each other. The apposed edges are then sutured, such as with the previously-described "Z" stitch pattern 190, to form the respective tubular structures 182, 184, 186 of a stent graft 188, as shown in FIG. 11B. Unlike the graft embodiment of FIGS. 11A-11F, the stitching pattern that transforms the planar swatch to a tubular structure is located on the side branch side, i.e., the "top", of the main graft lumen 182, and extends along the lengths on both sides of the side branch lumens 184, 186.

Figure 14:
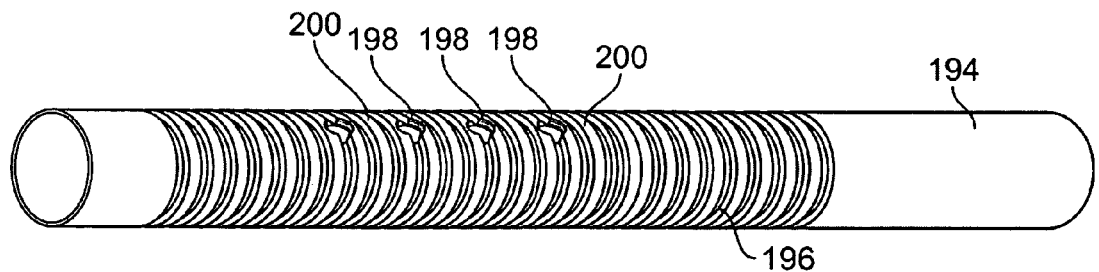
FIG. 14 illustrates another mandrel apparatus of the present invention for forming the convolution pattern in the graft of FIG. 13D.

Once the graft structure 188 is provided, convolutions 190 may then be formed in the graft material as substantially described above with respect to FIG. 11F, but with a slight variation in order to preserve the diameter at the base of each of the side branch lumens 184. Specifically, as illustrated in FIG. 14, the mandrel device 194 used has voids 200 in the convolution pattern 196 about each of the threaded bore holes 198 for receiving the side branch lumen mandrels (not shown). As such, the resulting convolution pattern formed within the graft material 182 provides corresponding areas 202 about the perimeter of the base of each of the side branch lumens 184, 186 which are devoid of convolutions. Forming convolutions, i.e., pleating the material, at these base areas would otherwise reduce the overall perimeter, and thus the diameter, of the side branch lumens. As previously discussed, an additional yet optional radiopaque stitching pattern 192 may be placed within graft 188, running longitudinally along the main lumen 182 and positioned approximately 180° about the circumference from stitching pattern 190. As such both the "top" and "bottom" sides of graft 188 are provided with a radiopaque marking to facilitate alignment of the graft within the delivery sheath as well as within the vasculature.

Upon final preparation of the graft by any method, the graft is engaged and affixed to the stent (not shown) to form the combined stent graft. The graft material may be positioned on either the outer or inner surface of the stent, or two graft layers may be used to encase the stent structure in between. For stent grafts in which the graft is external to the stent, the combined structure is formed by stretching the stent along its length and, while in the stretched condition, inserted it into one end of the main lumen of the graft. The stent is pulled there through and its side branches are aligned with the corresponding side branch lumens of the graft which and positioned therein. Once properly aligned, the stent is released from its stretched condition and allowed to expand into the graft to form a snug fit between the two. For stent grafts in which the graft is internal to the stent structure, graft is folded or otherwise compressed and drawing through the main lumen of the stent. The position of the graft is adjusted to align the side branch lumens of the graft with the corresponding side branch lumens of the stent, and then the side lumens of the graft are pulled or pushed through the side lumens of the stent.

Each of these variations has its advantages. Specifically, with the graft external to the stent, the graft material ensures apposition and sealing between the stent graft and the vessel wall, thereby minimizing the risk of endoleak. Having the graft internal to the stent ensures a non-thrombogenic blood flow pathway through the stent graft. A stent graft employing both an inner and outer graft covering clearly provides advantages of both embodiments, however, with a potential increase in the bulkiness of the device that may require larger delivery system.

The stent may be further anchored to the graft by a coating or by mechanical means, for example, by screws, cements, fasteners, sutures or staples or by friction. Further, mechanical attachment means may be employed to effect attachment to the implant site by including in the design of the stent a means for fastening it into the surrounding tissue. For example, the device may include metallic spikes, anchors, hooks, barbs, pins, clamps, or a flange or lip to hold the stent in place.

The graft portion of a stent graft may be made from a textile, polymer, latex, silicone latex, polyetraflouroethylene, polyethylene, Dacron polyesters, polyurethane silicon polyurethane copolymers or other or suitable material such as biological tissue. The graft material must be flexible and durable in order to withstand the effects of installation and usage. One of skill in the art would realize that grafts of the subject invention may be formulated by many different well known methods such as for example, by weaving or formed by dipping a substrate in the desired material.

Biological tissues that may be used to form the graft material (as well as the stent) include, but are not limited to, extracellular matrices (ECMs), acellularized uterine wall, decellularized sinus cavity liner or membrane, acellular ureture membrane, umbilical cord tissue, decelluarized pericardium and collagen. Suitable ECM materials are derived from mammalian hosts sources and include but are not limited to small intestine submucosa, liver basement membrane, urinary bladder submucosa, stomach submucosa, the dermis, etc. Extracellular matrices suitable for use with the present invention include mammalian small intestine submucosa (SIS), stomach submucosa, urinary bladder submucosa (UBS), derails, or liver basement membranes derived from sheep, bovine, porcine or any suitable mammal.

Submucosal tissues (ECMs) of warm-blooded vertebrates are useful in tissue grafting materials. Submucosal tissue graft compositions derived from small intestine have been described in U.S. Pat. No. 4,902,508 (hereinafter the '508 patent) and U.S. Pat. No. 4,956,178 (hereinafter the '178 patent), and submucosal tissue graft compositions derived from urinary bladder have been described in U.S. Pat. No. 5,554,389 (hereinafter the '389 patent). All of these (ECMs) compositions are generally comprised of the same tissue layers and are prepared by the same method, the difference being that the starting material is small intestine on the one hand and urinary bladder on the other. The procedure detailed in the '508 patent, incorporated by reference in the '389 patent and the procedure detailed in the '178 patent, includes mechanical abrading steps to remove the inner layers of the tissue, including at least the lumenal portion of the tunica mucosa of the intestine or bladder, i.e., the lamina epithelialis mucosa (epithelium) and lamina propria, as detailed in the '178 patent. Abrasion, peeling, or scraping the mucosa delaminates the epithelial cells and their associated basement membrane, and most of the lamina propria, at least to the level of a layer of organized dense connective tissue, the stratum compactum. Thus, the tissue graft material (ECMs) previously recognized as soft tissue replacement material is devoid of epithelial basement membrane and consists of the submucosa and stratum compactum.

Examples of a typical epithelium having a basement membrane include, but are not limited to the following: the epithelium of the skin, intestine, urinary bladder, esophagus, stomach, cornea, and liver. The epithelial basement membrane may be in the form of a thin sheet of extracellular material contiguous with the basilar aspect of epithelial cells. Sheets of aggregated epithelial cells of similar type form an epithelium. Epithelial cells and their associated epithelial basement membrane may be positioned on the lumenal portion of the tunica mucosa and constitute the internal surface of tubular and hollow organs and tissues of the body. Connective tissues and the submucosa, for example, are positioned on the abluminal or deep side of the basement membrane. Examples of connective tissues used to form the ECMs that are positioned on the abluminal side of the epithelial basement membrane include the submucosa of the intestine and urinary bladder (UBS), and the dermis and subcutaneous tissues of the skin. The submucosa tissue may have a thickness of about 80 micrometers, and consists primarily (greater than 98%) of a cellular, eosinophilic staining (H&E stain) extracellular matrix material. Occasional blood vessels and spindle cells consistent with fibrocytes may be scattered randomly throughout the tissue. Typically the material is rinsed with saline and optionally stored in a frozen hydrated state until used.

Fluidized UBS, for example, can be prepared in a manner similar to the preparation of fluidized intestinal submucosa, as described in U.S. Pat. No. 5,275,826 the disclosure of which is expressly incorporated herein by reference. The UBS is comminuted by tearing, cutting, grinding, shearing or the like. Grinding the UBS in a frozen or freeze-dried state is preferred although good results can be obtained as well by subjecting a suspension of submucosa pieces to treatment in a high speed (high shear) blender and dewatering, if necessary, by centrifuging and decanting excess water. Additionally, the comminuted fluidized tissue can be solubilized by enzymatic digestion of the bladder submucosa with a protease, such as trypsin or pepsin, or other appropriate enzymes for a period of time sufficient to solubilize said tissue and form a substantially homogeneous solution.

The coating for the stent may be powder forms of UBS. In one embodiment a powder form of UBS is prepared by pulverizing urinary bladder submucosa tissue under liquid nitrogen to produce particles ranging in size from 0.1 to 1 mm$^2$. The particulate composition is then lyophilized overnight and sterilized to form a solid substantially anhydrous particulate composite. Alternatively, a powder form of UBS ear be formed from fluidized UBS by drying the suspensions or solutions of comminuted UBS.

Other examples of ECM material suitable for use with the present invention include but are not limited to fibronectin, fibrin, fibrinogen, collagen, including fibrillar and non-fibrillar collagen, adhesive glycoproteins, proteoglycans, hyaluronan, secreted protein acidic and rich in cysteine (SPARC), thrombospondins, tenacin, and cell adhesion molecules, and matrix metalloproteinase inhibitors.

The stent may be processed in such a way as to adhere an ECM covering (or other material) to only the wire, and not extend between wire segments or within the stent cells. For instance, one could apply energy in the form of a laser beam, current or heat to the wire stent structure while the ECM has been put in contact with the underlying structure. Just as when cooking meat on a hot pan leaves tissue, the ECM could be applied to the stent in such a manner.

Subsequent to implant of the subject devices, the ECM portion of the implant is eventually resorbed by the surrounding tissue, taking on the cellular characteristics of the tissue, e.g., endothelium, smooth muscle, adventicia, into which it has been resorbed. Still yet, an ECM scaffolding having a selected configuration may be operatively attached to a stent or stent graft of the present invention at a selected location whereby the ECM material undergoes subsequent remodeling to native tissue structures at the selected location. For example, the ECM scaffolding may be positioned at the annulus of a previously removed natural aortic valve configured in such a way as to create the structural characteristics of aortic valve leaflets and whereby the implant provides valve function.

The subject stents, grafts and/or stent grafts may be coated in order to provide for local delivery of a therapeutic or pharmaceutical agent to the disease site. Local delivery requires smaller dosages of therapeutic or pharmaceutical agent delivered to a concentrated area; in contrast to systemic dosages which require multiple administrations and loss of material before reaching the targeted disease site. Any therapeutic material, composition or drug, may be used including but not limited to, dexamethasone, tocopherol, dexamethasone phosphate, aspirin, heparin, coumadin, urokinase, streptokinase and TPA, or any other suitable thrombolytic substance to prevent thrombosis at the implant site. Further therapeutic and pharmacological agents include but are not limited to tannic acid mimicking dendrimers used as submucosa stabilizing nanomordants to increase resistance to proteolytic degradation as a means to prevent post-implantational aneurysm development in decellularized natural vascular scaffolds, cell adhesion peptides, collagen mimetic peptides, hepatocyte growth factor, proliverative/antimitotic agents, paclitaxel, epidipodophyllotoxins, antibiotics, anthracyclines, mitoxantrone, bleomycins, plicamycin, and mitomycin, enzymes, antiplatelet agents, nonsteroidal agents, heteroaryl acetic acids, gold compounds, immunosuppressives, angiogenic agents, nitric oxide donors, antisense oligonucleotides, cell cycle inhibitors, and protease inhibitors.

For purposes of agent delivery, the subject stents, grafts and/or stent grafts are coated with a primer layer onto a surface. The primer layer formulates a reservoir for containing the therapeutic/pharmaceutical agent. The overlapping region between the primer layer and active ingredient may be modified to increase the permeability of the primer layer to the active ingredient. For example, by applying a common solvent, the active ingredient and the surface layer mix together and the active ingredient gets absorbed into the primer layer. In addition, the primer layer may also be treated to produce an uneven or roughened surface. This rough area entraps the active ingredient and enhances the diffusion rate of the ingredient when the stent is inserted into the patient's body. As such, the implant has the ability to diffuse drugs or other agents at a controllable rate. Furthermore, one of skill in the art would understand that the subject invention may provide a combination of multiple coatings, such as the primer layer may be divided into multiple regions, each containing a different active ingredient.

The subject implants may also be seeded with cells of any type including stem cells, to promote angiogenesis between the implant and the arterial walls. Methods have included applying a porous coating to the device which allows tissue growth into the interstices of the implant surface. Other efforts at improving host tissue in growth capability and adhesion of the implant to the host tissue have involved including an electrically charged or ionic material in the tissue-contacting surface of the device.

The stent, graft, or stent graft of the present invention may also include a sensor or sensors to monitor pressure, flow, velocity, turbidity, and other physiological parameters as well as the concentration of a chemical species such as for example, glucose levels, pH, sugar, blood oxygen, glucose, moisture, radiation, chemical, ionic, enzymatic, and oxygen. The sensor should be designed to minimize the risk of thrombosis and embolization. Therefore, slowing or stoppage of blood flow at any point within the lumen must be minimized. The sensor may be directly attached to the outer surface or may be included within a packet or secured within the material of the stent, graft, or stent graft of the present invention. The biosensor may further employ a wireless means to deliver information from the implantation site to an instrument external to the body.

The stent, graft or stent graft may be made of visualization materials or be configured to include marking elements, which provide an indication of the orientation of the device to facilitate proper alignment of the stent at the implant site. Any suitable material capable of imparting radio-opacity may be used, including, but not limited to, barium sulfate, bismuth trioxide, iodine, iodide, titanium oxide, zirconium oxide, metals such as gold, platinum, silver, tantalum, niobium, stainless steel, and combinations thereof. The entire stent or any portion thereof may be made of or marked with a radiopaque material, i.e., the crowns of the stent.

Figure 9:
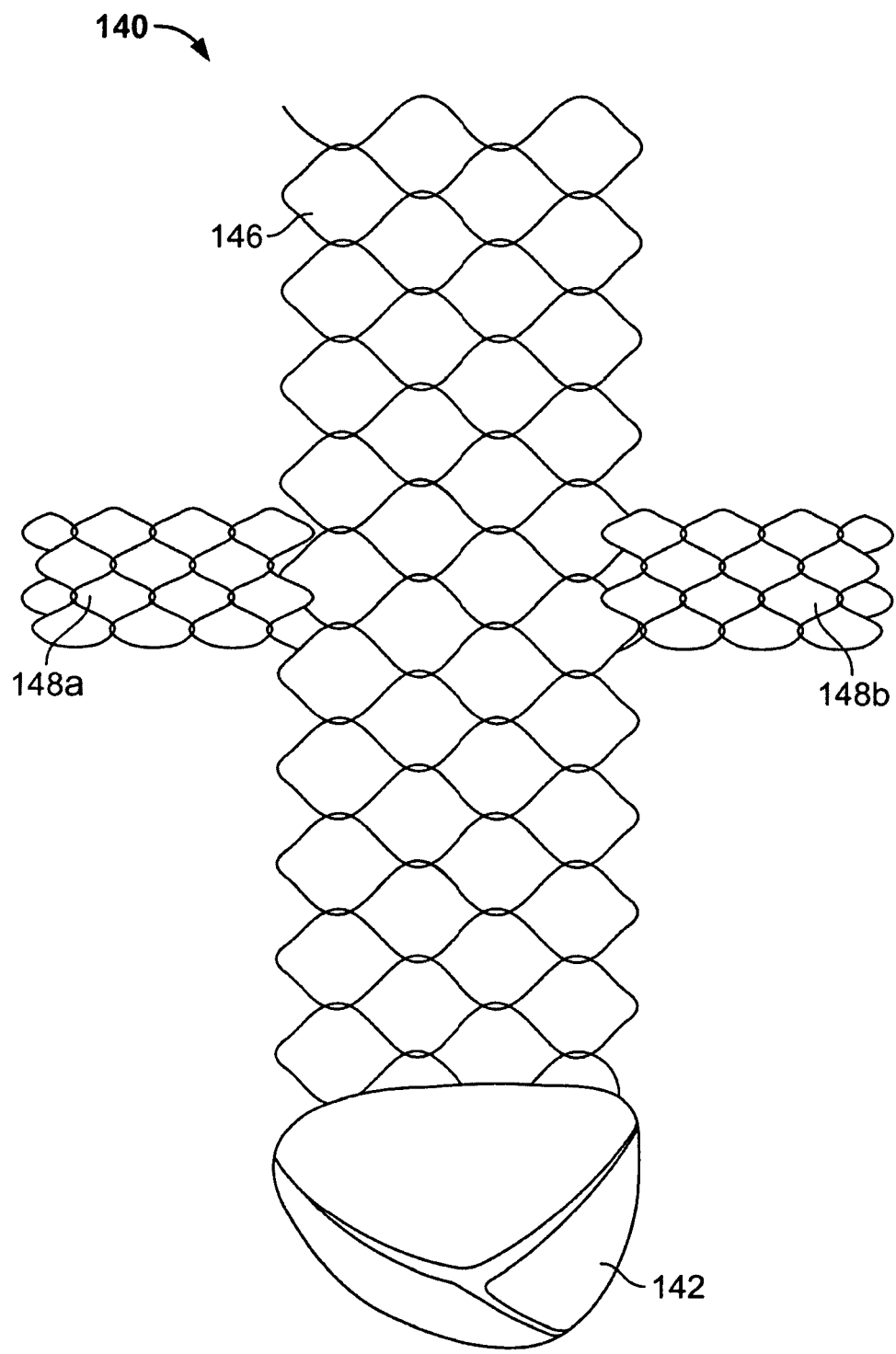
FIG. 9 illustrates another embodiment of an implant of the present invention having a cardiac valve operatively coupled to it.

It is also contemplated that therapeutic or diagnostic components or devices may be integrated with the subject implants. Such devices may include but are not limited to prosthetic valves, such as cardiac valves (e.g., an aortic or pulmonary valve) and venous valves, sensors to measure flow, pressure, oxygen concentration, glucose concentration, etc., electrical pacing leads, etc. For example, as illustrated in FIG. 9, an implant 140 for treating the aortic root is provide which includes a mechanical or biological prosthetic valve 142 employed at a distal end of the main lumen 146. Device 140 further includes two smaller, generally opposing side branch lumens 148a and 148b adjustably aligned for placement within the right and left coronary ostia, respectively. The length of the stent graft may be selected to extend to a selected distance where it terminates at any location prior to within or subsequent to the aortic arch, e.g., it may extend into the descending aorta. Any number of additional side branches may be provided for accommodating the aortic arch branch vessels.

Those skilled in the art will appreciate that any suitable stent or graft configuration may be provided to treat other applications at other vascular locations at or near the intersection of two or more vessels (e.g., bifurcated, trifurcated, quadrificated, etc.) including, but not limited to, the aortoilliac junction, the femoral-popiteal junction, the brachycephalic arteries, the posterior spinal arteries, coronary bifurcations, the carotid arteries, the superior and inferior mesenteric arteries, general bowel and stomach arteries, cranial arteries and neurovascular bifurcations.

The devices of the present invention are deliverable through endovascular or catheter-based approaches whereby the device is positioned within a delivery system in a reduced shape and size and caused to expand to an expanded shape and dimension upon deployment from the system. The devices may be designed to be self-expanding upon release from a delivery system, i.e., catheter or sheath, or may require active expansion by separate means, such as a balloon or other expandable or inflatable devices. Still yet, other devices may be deployable with a combination of a passive and active deployment system. Any suitable stent delivery technique may be employed to deliver the stents, grafts and stent grafts of the present invention, where those skilled in the art will recognize certain features that may be made to the stent, graft or stent graft to accommodate a particular deployment method.

For example, self-expanding devices of the present invention are typically fabricated from materials that may be superelastic materials, such as nickel-titanium alloys, spring steel, and polymeric materials. Alternatively or additionally, the particular weave pattern used to form the cells of the device incorporates a radial spring force that self-expands upon release from a delivery system.

If more control is desired in deployment of self-expanding devices, the devices may be configured for delivery and deployment by use of one or more designated deployment members, including but not limited to lines, strings, filaments, fibers, wires, stranded cables, tubings, etc. The deployment members are releasably attached to the device, such as by being looped through one or more apices of the device, and used to retain the device in a constrained condition as well as to release the device from the constrained condition. More particularly, the deployment members may be selectively tensioned, pulled and/or released to release the apices and deploy the device. Examples of such stent delivery systems are disclosed in U.S. Pat. No. 6,099, 548, U.S. Patent Publication Nos. 2006/0129224 and 2006/ 0155366, and co-pending U.S. patent application Ser. No. 11/539,478 filed Oct. 6, 2006 and U.S. patent application 60/889,186 filed contemporaneously herewith, both entitled Apparatus and Method for Deploying an Implantable Device Within the Body and incorporated herein by reference.

Other means of releasable attachment which may be employed with the delivery systems to deploy the subject devices include but are not limited to electrolytic erosion, thermal energy, magnetic means, chemical means, mechanical means or any other controllable detachment means.

In some applications, active deployment systems including expandable balloons and the like may also be used to deploy the stents of the present invention. Examples of balloon expandable stent delivery systems are disclosed in U.S. Pat. Nos. 6,942,640, 7,056,323, 7,070,613 and 7,105, 014.

It is also contemplated that the implantable devices may be delivered by use of a delivery system that enables partial deployment of the device prior to full deployment in order to facilitate proper placement of the device. Additionally, the selected delivery system may provide for the individual and independent deployment of each lumenal end of the implantable devices, where some or all of the lumenal ends may be simultaneously deployed or serially deployed in an order that best facilitates the implantation procedure.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present, invention is embodied by the appended claims.

It must be noted that as used herein and in the appended claims, the singular forms "a", "an", and "the" include plural referents unless the context clearly dictates otherwise. Thus, for example, reference to "a wire" may include a plurality of such wires and reference to "the stent lumen" includes reference to one or more stent lumens and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject, to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

That which is claimed is:

1. An implantable stent for use in a vessel or tubular structure, comprising:
   a main lumen comprising a structure formed from wires and having a uniform diameter and having a pattern of interconnected cells;
   at least one side branch lumen formed from wires and extending laterally to the structure and where an angle between the side branch lumen and the main lumen is adjustable, and where the wires forming the main lumen and wires forming the side branch lumen are interconnected allowing the side branch lumen to be in fluid communication with the main lumen; and
   a graft material coupled to the main lumen and extending along a length of the main lumen and the at least one side branch lumen, where the graft lumen includes a series of convolutions extending along a length of the main lumen and having pre-formed ridges and grooves about an entire circumference of the graft, where the series of convolutions enhances flexibility and adjustability of the implantable stent where a perimeter of a base of the at least one side branch lumen that connects to the main lumen is devoid of convolutions.

2. The implantable stem of claim 1, wherein the structure comprises one or more length sections having cells having a first size and one or more other sections having cells having a second or size, wherein the first size is greater than the second size.

3. The implantable stem of claim 1, wherein the main lumen has at least one section of smaller cells adjacent the side branch lumen.

4. The implantable stem of claim 1, wherein at least one side branch lumen comprises two side branch lumens and the at least one section of smaller cells extends between the two side branch lumens.

5. The implantable stent of claim 4, wherein the stem is made of stainless steel, elgiloy, tungsten, platinum or NITINOL.

6. The implantable stem of claim 1, wherein the cell size of the at least one side branch lumens is gradually reduced in the distal direction.

7. The implantable stem of claim 1, wherein the structure is constructed of elastically compliant wire.

8. The implantable stem of claim wherein the structure comprises a main lumen and at least one side branch lumen extending laterally to the structure.

9. The implantable stem of claim 8, wherein the cell size of the at least one side branch lumens is gradually reduced in the distal direction.

10. The implantable stent of claim 8, wherein the structure is constructed of elastically compliant wire.

11. The implantable stent of claim 10, wherein the stent is made of stainless steel, elgiloy, tungsten, platinum or NITINOL.

12. The implantable stent of claim 1, wherein the structure comprises two side branch lumens.

13. The implantable stem of claim 1, where the size of the cells varies along a length of the structure.

* * * * *